United States Patent
Park et al.

(10) Patent No.: US 12,371,453 B2
(45) Date of Patent: Jul. 29, 2025

(54) POLYPEPTIDE HAVING ANTIBACTERIAL ACTIVITY, COMPOSITION FOR PREVENTING OR TREATING SEPSIS COMPRISING SAME, AND ANTIBACTERIAL COMPOSITION

(71) Applicant: HLB SCIENCE INC., Seoul (KR)

(72) Inventors: Yeong Min Park, Seoul (KR); Yangmee Kim, Seoul (KR); In Duk Jung, Chungcheongbuk-do (KR); Seung-Hyun Lee, Seoul (KR)

(73) Assignee: HLB SCIENCE INC., Seoul (KR)

( * ) Notice: Subject to any disclaimer, the term of this patent is extended or adjusted under 35 U.S.C. 154(b) by 784 days.

(21) Appl. No.: 17/434,538

(22) PCT Filed: Feb. 27, 2020

(86) PCT No.: PCT/KR2020/002826
§ 371 (c)(1),
(2) Date: Aug. 27, 2021

(87) PCT Pub. No.: WO2020/175936
PCT Pub. Date: Sep. 3, 2020

(65) Prior Publication Data
US 2022/0144892 A1    May 12, 2022

(30) Foreign Application Priority Data

Feb. 28, 2019  (KR) .................. 10-2019-0023534
Feb. 26, 2020  (KR) .................. 10-2020-0023629

(51) Int. Cl.
*C07K 7/06*   (2006.01)
*A61K 38/00*  (2006.01)
(Continued)

(52) U.S. Cl.
CPC ............... *C07K 7/06* (2013.01); *A61P 31/04* (2018.01); *C07K 7/08* (2013.01); *A61K 38/00* (2013.01)

(58) Field of Classification Search
CPC . C07K 7/06; C07K 7/08; C07K 1/042; C07K 1/14; A23L 33/18; A23V 2200/322;
(Continued)

(56) References Cited

U.S. PATENT DOCUMENTS 7,608,277 B2 * 10/2009 Roth ...................... C07K 14/35
424/234.1
10,066,009 B2    9/2018 Kovacevich et al.
(Continued)

FOREIGN PATENT DOCUMENTS

JP    2014-520149 A    8/2014
KR    10-1477795 B1    1/2015
(Continued)

OTHER PUBLICATIONS

Vagner et al., Peptidomimetics, a synthetic tool of drug discovery. Curr Opin Chem Biol. Jun. 2008;12(3):292-6. doi: 10.1016/j.cbpa.2008.03.009. Epub May 14, 2008. PMID: 18423417; PMCID: PMC2515564 (Year: 2008).*
(Continued)

*Primary Examiner* — Randall L Beane
(74) *Attorney, Agent, or Firm* — Riverside Law LLP

(57) ABSTRACT

The present invention provides: a peptide having antibacterial activity; a composition for preventing or treating sepsis comprising same; and an antibacterial composition. More specifically, the peptide according to the present invention has the excellent effects of not only suppressing the growth of bacteria but removing endotoxins derived from bacteria, thus exhibiting an excellent therapeutic effect on sepsis, and thus can be usefully used to prevent or treat sepsis. In
(Continued)

addition, the peptide according to the present invention has selectively excellent antibacterial activity against Gram positive/negative bacteria, and thus can be usefully used in an antibacterial composition for Gram-positive/negative bacteria, or to prevent or treat various infectious diseases caused by Gram-positive/negative bacteria. Furthermore, the peptide according to the present invention exhibits excellent resistance against proteolytic enzymes, and is highly stable, and thus is expected to be utilized in various forms, such as a pharmaceutical composition, a cosmetic composition, a food composition, a health food composition, a feed composition, and a quasi-drug composition.

15 Claims, 8 Drawing Sheets

Specification includes a Sequence Listing.

(51) Int. Cl.
*A61P 31/04* (2006.01)
*C07K 7/08* (2006.01)

(58) Field of Classification Search
CPC ........ A61K 38/00; A61K 38/08; A61K 38/10; A61P 25/28; A61P 31/04; C12N 9/12; Y02E 50/30
See application file for complete search history.

(56) References Cited

U.S. PATENT DOCUMENTS

| | | | |
|---|---|---|---|
| 2011/0217244 A1 | 9/2011 | Johnston | |
| 2023/0287048 A1* | 9/2023 | Jung | C07K 1/14 |
| 2024/0082345 A1* | 3/2024 | Park | A61K 38/10 |

FOREIGN PATENT DOCUMENTS

| | | |
|---|---|---|
| KR | 10-2016-0070880 A | 6/2016 |
| KR | 10-2016-0108560 A | 9/2016 |
| KR | 10-2016-0118994 A | 10/2016 |
| KR | 10-1792239 B1 | 10/2017 |
| WO | 2018-236873 A1 | 12/2018 |
| WO | 2021187928 A1 | 9/2021 |

OTHER PUBLICATIONS

Goto et al., Initiating translation with D-amino acids. RNA. Jul. 2008;14(7):1390-8. doi: 10.1261/rna.1020708. Epub May 30, 2008. PMID: 18515548; PMCID: PMC24419 (Year: 2008).*

Wals et al., Unnatural amino acid incorporation in *E. coli*: current and future applications in the design of therapeutic proteins. Front Chem. Apr. 1, 2014;2:15. doi: 10.3389/fchem.2014.00015. PMID: 24790983; PMCID: PMC3982533 (Year: 2014).*

New Insight into leading viral cause of congenital birth defects, sciencedaily.com, 2 pages (Apr. 4, 2017), also available at https://www.sciencedaily.com/releases/2017/04/170404104751.htm# (last visited May 10, 2024) (Year: 2017).*

Azevedo et al., The effect of antibacterial and non-antibacterial compounds alone or associated with antifugals upon fungi. Front Microbiol. Jul. 3, 2015;6:669. doi: 10.3389/fmicb.2015.00669. PMID: 26191055; PMCID: PMC4490243 (Year: 2015).*

"Infection", Merriam-webster.com, 5 pages, Jan. 2022, also available at https://www.merriam-webster.com/dictionary/infection (last visited Jan. 24, 2022) (Year: 2022).*

Australian Examination Report issued in App. No. AU2020227591, dated Feb. 21, 2022, 7 pages.

International Search Report for PCT/KR2020/002826 dated Jun. 12, 2020 (pp. 1-4).

* cited by examiner

SEQUENCE LISTING

```
<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: FP1(WT)

<400> SEQUENCE: 1

Lys Leu Gly Val Glu Ala Lys Arg Tyr Leu Asp
1               5                   10

<210> SEQ ID NO 2
<211> LENGTH: 11
<212> TYPE: PRT
<213> ORGANISM: Artificial Sequence
<220> FEATURE:
<223> OTHER INFORMATION: FP3

<400> SEQUENCE: 2
```

```
Lys Leu Gly Val Glu Ala Lys Arg Tyr Leu Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: FP5

<400> SEQUENCE: 3

Leu Arg Leu Gly Val Glu Ala Lys Arg Tyr Leu Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: FP6

<400> SEQUENCE: 4

Leu Arg Leu Gly Val Glu Leu Lys Arg Tyr Leu Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: FP9

<400> SEQUENCE: 5

Lys Leu Gly Val Glu Ala Leu Arg Tyr Leu Asp
1               5                   10

<210> SEQ ID NO 6
<211> LENGTH: 11
<212> TYPE: PRT
<213> ORGANISM: Artificial Sequence
<220> FEATURE:
<223> OTHER INFORMATION: FP12-NH2

<400> SEQUENCE: 6

Arg Leu Arg Val Lys Leu Arg Arg Tyr Leu Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: FP13-NH2

<400> SEQUENCE: 7

Lys Leu Arg Val Lys Leu Arg Arg Tyr Leu Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: allD FP12-NH2

<400> SEQUENCE: 8

Arg Leu Arg Val Lys Leu Arg Arg Tyr Leu Arg
```

```
<210> SEQ ID NO 9
<211> LENGTH: 11
<212> TYPE: PRT
<213> ORGANISM: Artificial Sequence
<220> FEATURE:
<223> OTHER INFORMATION: allD FP13-NH2

<400> SEQUENCE: 9

Lys Leu Arg Val Lys Leu Arg Arg Tyr Leu Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: allD FP-13-9a-NH2

<400> SEQUENCE: 10

Lys Leu Arg Val Lys Leu Arg Arg Ala Leu Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: allD FP-13-9w-NH2

<400> SEQUENCE: 11

Lys Leu Arg Val Lys Leu Arg Arg Trp Leu Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: allD FP-13-9k-NH2

<400> SEQUENCE: 12

Lys Leu Arg Val Lys Leu Arg Arg Lys Leu Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: allD FP13-NH2 (AcOH)

<400> SEQUENCE: 13

Lys Leu Arg Val Lys Leu Arg Arg Tyr Leu Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: PEG-allD FP13-NH2 (AcOH)

<400> SEQUENCE: 14

Lys Leu Arg Val Lys Leu Arg Arg Tyr Leu Arg
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: FP12

<400> SEQUENCE: 15

Arg Leu Arg Val Lys Leu Arg Arg Tyr Leu Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: FP13

<400> SEQUENCE: 16

Lys Leu Arg Val Lys Leu Arg Arg Tyr Leu Arg
1               5                   10

<210> SEQ ID NO 17
<211> LENGTH: 11
<212> TYPE: PRT
<213> ORGANISM: Artificial Sequence
<220> FEATURE:
<223> OTHER INFORMATION: allD FP21-NH2

<400> SEQUENCE: 17

Arg Leu Arg Val Lys Leu Arg Arg Trp Leu Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: allD FP-13-9d-NH2

<400> SEQUENCE: 18

Lys Leu Arg Val Lys Leu Arg Arg Asp Leu Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Ln-X1-L-X2-V-X3-X4-X5-R-X6-L-X7
<220> FEATURE:
<221> NAME/KEY: SITE
<222> LOCATION: (1)
<223> OTHER INFORMATION: n is 0 or 1
<220> FEATURE:
<221> NAME/KEY: VARIANT
<222> LOCATION: (2)
<223> OTHER INFORMATION: X1 is lysine (K) or arginine (R)
<220> FEATURE:
<221> NAME/KEY: VARIANT
<222> LOCATION: (4)
<223> OTHER INFORMATION: X2 is glycine (G) or arginine (R)
<220> FEATURE:
<221> NAME/KEY: VARIANT
<222> LOCATION: (6)
<223> OTHER INFORMATION: X3 is glutamic acid (E) or lysine (K)
<220> FEATURE:
<221> NAME/KEY: VARIANT
<222> LOCATION: (7)

```
<223> OTHER INFORMATION: X4 is alanine (A) or leucine (L)
<220> FEATURE:
<221> NAME/KEY: VARIANT
<222> LOCATION: (8)
<223> OTHER INFORMATION: X5 is lysine (K), leucine (L) or arginine (R)
<220> FEATURE:
<221> NAME/KEY: VARIANT
<222> LOCATION: (10)
<223> OTHER INFORMATION: X6 is tyrosine (Y), alanine (A), tryptophan
      (W), lysine (K) or aspartic acid (D)
<220> FEATURE:
<221> NAME/KEY: VARIANT
<222> LOCATION: (12)
<223> OTHER INFORMATION: X7 is aspartic acid (D) or arginine (R)

<400> SEQUENCE: 19

Leu Xaa Leu Xaa Val Xaa Xaa Xaa Arg Xaa Leu Xaa
 1               5                  10
```

POLYPEPTIDE HAVING ANTIBACTERIAL ACTIVITY, COMPOSITION FOR PREVENTING OR TREATING SEPSIS COMPRISING SAME, AND ANTIBACTERIAL COMPOSITION

CROSS-REFERENCE TO RELATED APPLICATIONS

This application is a U.S. National Phase Application filed under 35 U.S.C. § 371 claiming benefit to International Patent Application No. PCT/KR2020/002826, filed Feb. 27, 2020, which claims the benefit of priority from Korean Patent Application No. 10-2019-0023534, filed on Feb. 28, 2019, and Korean Patent Application No. 10-2020-0023629, filed on Feb. 26, 2020, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0120-00US_Sequence_Listing_ST25v2.txt" in ASCII format. The text file containing the Sequence Listing of the present application was created on Aug. 2, 2024 and is 5,171 bytes in size.

STATEMENT REGARDING GOVERNMENT RIGHTS

The present invention was undertaken with the support of Completion of DD-S052 Preclinical Study and Preparation for Phase 1 Clinical Approval No. HI20C0384 grant funded by the Ministry of Health & welfare, Republic of Korea.

TECHNICAL FIELD

The present invention relates to a polypeptide having antibacterial activity, a composition for preventing or treating sepsis, which includes the same, and an antibacterial composition, and the like.

BACKGROUND ART

Sepsis is an inflammatory response caused by excessive activation of the immune system of the body by lipopolysaccharide (LPS), which is a component of a cell wall, acting as a toxin when the body is infected by pathogenic gram-negative bacteria, and can cause infection in the whole body or can be accompanied by shock if there are severe symptoms. Specifically, sepsis is generally caused when patients with basic diseases such as malignant tumors, leukemia, malignant lymphoma, acquired immunodeficiency syndrome (AIDS), collagen disease, renal failure, liver disease, cerebrovascular disorders, and diabetes or weakly resistant hosts with humoral or cellular immunodeficiency, such as the elderly and premature infants undergo chemotherapy with adrenal steroids or antitumor drugs, radiation therapy such as cobalt irradiation, or treatment and surgery such as indwelling catheters, hemodialysis, organ transplantation and heart surgery. Sepsis has become the leading cause of death of patients admitted to the intensive care unit of a hospital, and is a very serious disease with a fatality rate of usually 30% or more. Despite the advances in medical technology, there are many cases of sepsis due to infection as a sequela of surgery worldwide, and infection of a person with weak immunity in the body, such as a newborn baby or the elderly, often develops to sepsis. Typically, it is known that neonatal sepsis occurs in approximately 3 out of 1,000 full-term infants, and the incidence thereof increases 3 to 4-fold in premature infants.

While sepsis is usually treated with antibiotics, it cannot be effectively treated only with antibiotics in the case of treatment being delayed such that a large amount of bacteria have proliferated or in the case of infection by a strain having resistance to antibiotics, and the number of pathogens resistant to various antibiotics is gradually increasing. For this reason, there is an urgent demand for the development of a novel sepsis therapeutic agent.

Meanwhile, antimicrobial-resistant bacteria refer to bacteria that are resistant to a specific antibacterial agent and thus the agent does not work. For example, the antimicrobial-resistant bacteria include penicillin-resistant *Staphylococcus aureus*, which causes penicillin to be completely ineffective. In addition, Methicillin-Resistant *Staphylococcus aureus* (MRSA), which was first reported in academia in 1961 and has become a major pathogenic infectious bacterium worldwide, is known, and vancomycin-resistant *enterococcus* (VRE) was first found in Europe in 1988. In addition, vancomycin-resistant *Staphylococcus aureus* (VRSA) exhibiting high resistance to vancomycin, known as the final therapeutic agent for *Staphylococcus aureus*, which is the most common cause of human infection, was first reported by the US Centers for Disease Control and Prevention in 2002. Taking all of the above together, it can be seen that the spread of so-called super bacteria is highly increasing.

DISCLOSURE

Technical Problem

Therefore, as a result of repeated research to meet the above-described demands, the inventors confirmed that a peptide having a specific amino acid sequence is effective in inhibiting bacterial proliferation as well as in treating sepsis due to an excellent effect of removing an endotoxin isolated from dead bacteria, and selectively exhibits excellent antibacterial activity against gram-positive/negative bacteria, and thus the present invention was completed.

Accordingly, technical problems to be solved in the present invention are directed to providing a peptide having antibacterial activity, a composition for preventing or treating sepsis, which includes the same, and an antibacterial composition, and the like.

However, technical problems to be solved in the present invention are not limited to the above-described ones, and other problems which are not described herein will be fully understood by those of ordinary skill in the art from the following descriptions.

Technical Solution

To achieve the purpose of the present invention, the present invention provides a polypeptide represented by the following general sequence formula:

$$\text{L}_n\text{-X}_1\text{-L-X}_2\text{-V-X}_3\text{-X}_4\text{-X}_5\text{-R-X}_6\text{-L-X}_7 \text{(SEQ ID NO:19)} \quad \text{[General Formula]}$$

In the general formula,
n is 0 or 1;
L is leucine;
V is valine;
R is arginine;
X1 is lysine (K) or arginine (R);
X2 is glycine (G) or arginine (R);
X3 is glutamic acid (E) or lysine (K);
X4 is alanine (A) or leucine (L);
X5 is lysine (K) or arginine (R);
X6 is tyrosine (Y), alanine (A), tryptophan (W), lysine (K) or aspartic acid (D); and
X7 is aspartic acid (D) or arginine (R),
however, in the general formula, a polypeptide represented by the sequence of K-L-G-V-E-A-K-R-Y-L-D (SEQ ID NO:1) is excluded.

In one embodiment of the present invention, any one of 9 types of polypeptides consisting of 1) to 9) as follows is provided:
1) a polypeptide represented by the general formula, in which
n is 0;
X1 is lysine (K);
X2 is glycine (G);
X3 is glutamic acid (E);
X4 is alanine (A);
X5 is lysine (K);
X6 is tyrosine (Y), and
X7 is arginine (R);
2) a polypeptide represented by the general formula, in which
n is 1;
X1 is arginine (R);
X2 is glycine (G);
X3 is glutamic acid (E);
X4 is alanine (A);
X5 is lysine (K);
X6 is tyrosine (Y), and
X7 is arginine (R);
3) a polypeptide represented by the general formula, in which
n is 1;
X1 is arginine (R);
X2 is glycine (G);
X3 is glutamic acid (E);
X4 is leucine (L);
X5 is lysine (K);
X6 is tyrosine (Y), and
X7 is arginine (R);
4) a polypeptide represented by the general formula, in which
n is 0;
X1 is lysine (K);
X2 is glycine (G);
X3 is glutamic acid (E);
X4 is alanine (A);
X5 is leucine (L);
X6 is tyrosine (Y), and
X7 is aspartic acid (D);
5) a polypeptide represented by the general formula, in which
n is 0;
X1 is arginine (R);
X2 is arginine (R);
X3 is lysine (K);
X4 is leucine (L);
X5 is arginine (R);
X6 is tyrosine (Y), and
X7 is arginine (R);
6) a polypeptide represented by the general formula, in which
n is 0;
X1 is lysine (K);
X2 is arginine (R);
X3 is lysine (K);
X4 is leucine (L);
X5 is arginine (R);
X6 is tyrosine (Y), and
X7 is arginine (R);
7) a polypeptide represented by the general formula, in which
n is 0;
X1 is lysine (K);
X2 is arginine (R);
X3 is lysine (K);
X4 is leucine (L);
X5 is arginine (R);
X6 is alanine (A), and
X7 is arginine (R);
8) a polypeptide represented by the general formula, in which
n is 0;
X1 is lysine (K);
X2 is arginine (R);
X3 is lysine (K);
X4 is leucine (L);
X5 is arginine (R);
X6 is tryptophan (W), and
X7 is arginine (R); and
9) a polypeptide represented by the general formula, in which
n is 0;
X1 is lysine (K);
X2 is arginine (R);
X3 is lysine (K);
X4 is leucine (L);
X5 is arginine (R);
X6 is lysine (K), and
X7 is arginine (R).

In one embodiment of the present invention, the polypeptide refers to a peptidomimetic including an L-type peptide, a D-type peptide and a peptoid, or non-natural amino acids.

In one embodiment of the present invention, an end of the polypeptide is alkylated, PEGylated, or amidated.

In one embodiment of the present invention, an amine group ($NH_2$) is added to the C-terminus of the polypeptide.

In one embodiment of the present invention, the polypeptide has one or more of the following characteristics:
  binding ability to lipopolysaccharide (LPS) of gram-negative bacteria;
  selective disruption ability against bacterial cell membrane;
  resistance to proteolytic enzymes;
  cell membrane disruption ability against gram-positive bacteria; and
  binding ability to gram-positive bacteria-derived lipoteichoic acid (LTA) or lipoprotein (LPP).

In addition, the present invention provides an acetate salt substitution of trifluoroacetic acid (TFA) of a polypeptide represented by the general sequence formula.

In addition, the present invention provides a composition for preventing, alleviating or treating sepsis, which includes the polypeptide represented by the general sequence formula or an acetate salt substitution of trifluoroacetic acid thereof as an active ingredient.

In addition, the present invention provides a pharmaceutical/food/health food/cosmetic/quasi-drug/feed composition for preventing, alleviating or treating sepsis, which includes the polypeptide represented by the general sequence formula or an acetate salt substitution of trifluoroacetic acid thereof as an active ingredient.

The present invention provides a method of preventing or treating sepsis, which includes administering the polypeptide represented by the general sequence formula or an acetate salt substitution of trifluoroacetic acid thereof into a subject in need thereof.

In addition, the present invention provides a use of the polypeptide represented by the general sequence formula or an acetate salt substitution of trifluoroacetic acid thereof for preventing, alleviating or treating sepsis.

Further, the present invention provides a use of the polypeptide represented by the general sequence formula or an acetate salt substitution of trifluoroacetic acid thereof for preparing a preparation for preventing, alleviating or treating sepsis.

In addition, the present invention provides an antibacterial composition, which includes the polypeptide represented by the general sequence formula or an acetate salt substitution of trifluoroacetic acid thereof as an active ingredient.

In addition, the present invention provides an antibacterial pharmaceutical/food/health food/cosmetic/quasi-drug/feed composition, which includes the polypeptide represented by the general sequence formula or an acetate salt substitution of trifluoroacetic acid thereof as an active ingredient.

The present invention provides an antibacterial method, which includes administering the polypeptide represented by the general sequence formula or an acetate salt substitution of trifluoroacetic acid thereof into a subject in need thereof.

In addition, the present invention provides an antibacterial use of the polypeptide represented by the general sequence formula or an acetate salt substitution of trifluoroacetic acid thereof.

Further, the present invention provides a use of the polypeptide represented by the general sequence formula or an acetate salt substitution of trifluoroacetic acid thereof for preparing an antibacterial agent.

In one embodiment of the present invention, bacteria targeted by the antibacterial composition include one or more types selected from the group consisting of *Escherichia coli* DH5α, *Escherichia coli* K1, *Acinetobacter baumannii*, *Pseudomonas aeruginosa*, *Salmonella enteritidis*, *Salmonella typhimurium*, *Klebsiella pneumoniae*, *Staphylococcus aureus* and *Staphylococcus epidermidis*.

In one embodiment of the present invention, bacteria targeted by the antibacterial composition include one or more types of antibiotic-resistant bacteria selected from the group consisting of Extended Spectrum Beta Lactamase (ESBL)-resistant bacteria, carbapenem-resistant bacteria and Colistin-resistant bacteria.

In one embodiment of the present invention, the antibiotic-resistant bacteria include one or more types selected from the group consisting of ESBL (*E. coli*), carbapenem-resistant (CR)-*Acinetobactor baumannii*, CR-*Klebsiella pneumoniae*, CR-*Pseudomonas aeruginosa*, and Colistin-resistant *Acinetobactor baumannii*.

In addition, the present invention provides a composition for preventing, alleviating or treating an infectious disease, which includes the polypeptide represented by the general sequence formula or an acetate salt substitution of trifluoroacetic acid thereof as an active ingredient.

In addition, the present invention provides a pharmaceutical/food/health food/cosmetic/quasi-drug/feed composition for preventing, alleviating or treating an infectious disease, which includes the polypeptide represented by the general sequence formula or an acetate salt substitution of trifluoroacetic acid thereof as an active ingredient.

The present invention provides a method of preventing or treating an infectious disease, which includes administering the polypeptide represented by the general sequence formula or an acetate salt substitution of trifluoroacetic acid thereof into a subject in need thereof.

In addition, the present invention provides a use of the polypeptide represented by the general sequence formula or an acetate salt substitution of trifluoroacetic acid thereof for preventing, alleviating or treating an infectious disease.

Further, the present invention provides a use of the polypeptide represented by the general sequence formula or an acetate salt substitution of trifluoroacetic acid thereof for preparing a preparation for preventing, alleviating or treating an infectious disease.

In one embodiment of the present invention, the infectious disease is a gram-negative bacteria infection-related disease selected from the group consisting of pneumonia, peritonitis, meningitis, wound infection, osteoarthritis, cholecystitis, urinary tract infection, endocarditis, myocarditis, pericarditis, arthritis, pharyngitis, gonorrhea, bacterial dysentery, enteritis, conjunctivitis, gastritis, otitis media, cystitis, and lymphangitis.

In one embodiment of the present invention, the infection disease is gram-positive bacteria-infected disease selected from the group consisting of laryngopharyngitis, impetigo, rheumatic fever, glomerulonephritis, neonatal sepsis, meningitis, pharyngitis, pneumonia, endocarditis, scarlet fever, SSTI (skin and soft tissue infection), deep soft tissue infection, empyema, and vaginitis.

In addition, the present invention provides a polynucleotide encoding the polypeptide represented by the general sequence formula.

In addition, the present invention provides a recombinant vector including the polynucleotide.

In addition, the present invention provides a method of preparing a polypeptide represented by the general sequence formula, which includes culturing host cells transformed with the recombinant vector.

Advantageous Effects

A peptide according to the present invention has excellent effects of not only inhibiting the proliferation of standard bacteria and antibiotic-resistant bacteria, but also removing a bacteria-derived endotoxin, thereby exhibiting an excellent sepsis treatment effect, and when used in combination with an antibiotic, the peptide can minimize side effects caused by the antibiotic and thus can be effectively used in preventing or treating sepsis.

In addition, the peptide according to the present invention selectively has excellent antibacterial activity against gram-positive/negative bacteria, and thus can be effectively used in an antibacterial composition against gram-positive/negative bacteria or in preventing or treating various infectious diseases caused by gram positive/negative bacteria.

In addition, the peptide according to the present invention is not only safe for the human body, but also exhibits stability against a proteolytic enzyme, and thus can be used for a variety of purposes.

From top left to right, FP12-NH$_2$ (SEQ ID NO: 6)/all-D_FP12-NH$_2$ (SEQ ID NO: 8); and FP13-NH$_2$ (SEQ ID NO: 7)/allD FP13-NH$_2$ (SEQ ID NO: 9).

From bottom left to right, allD_FP13_9A (SEQ ID NO: 10)/allD_FP13_9D (SEQ ID NO: 18); and allD_FP13_9W (SEQ ID NO: 11)/allD_FP13_9K (SEQ ID NO: 12).

Figure 2:
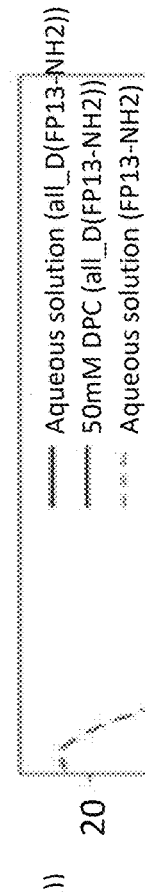
Figure 2:
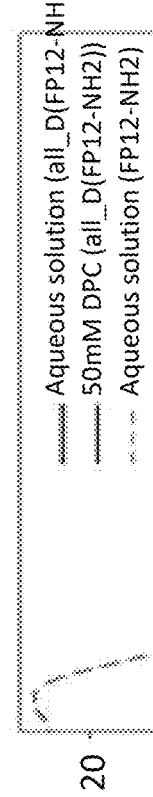

FIG. 2 is a set of graphs illustrating the result of measuring the secondary structures of peptides by circular polarization dichroism spectroscopy according to Example 5 of the present invention.

Figure 3:
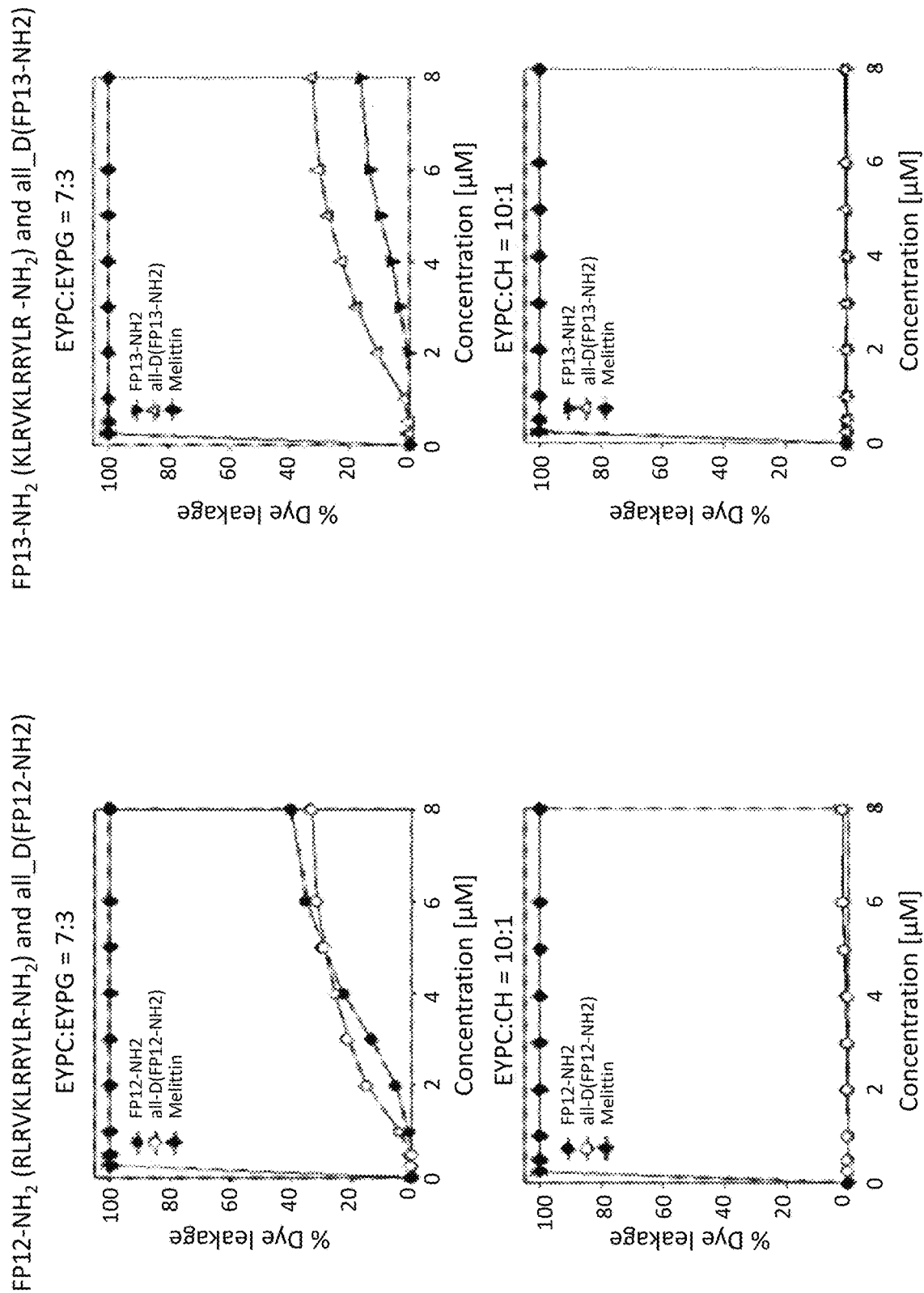

FIG. 3 is a set of graphs showing the result of measuring the disruption ability of peptides with respect to liposomes mimicking a bacterial cell membrane (top) and a red blood cell membrane (bottom) according to Example 6 of the present invention.

Figure 4:
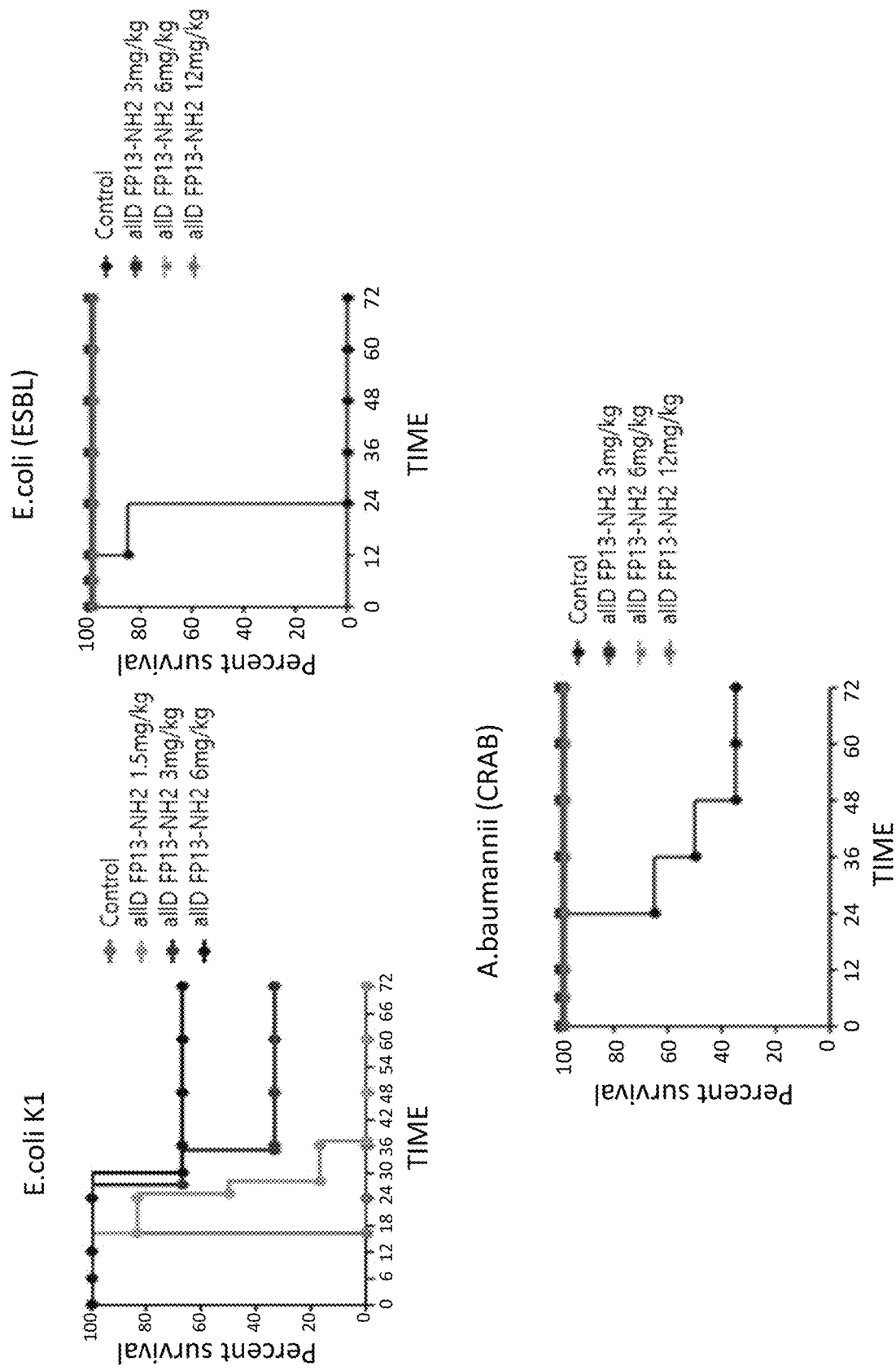

FIG. 4 illustrates the antibiotic effect of the allD FP13-NH$_2$ peptide according to Example 8 of the present invention. From left to right, the antibiotic effect of the allD FP13-NH$_2$ peptide against a standard strain *Escherichia coli* K1; the antibiotic effect of the allD FP13-NH$_2$ peptide against a clinical strain *Escherichia coli* (ESBL); and the antibiotic effect of the allD FP13-NH$_2$ peptide against a clinical strain carbapenem-resistant *Acinetobacter baummanii*.

Figure 5A:
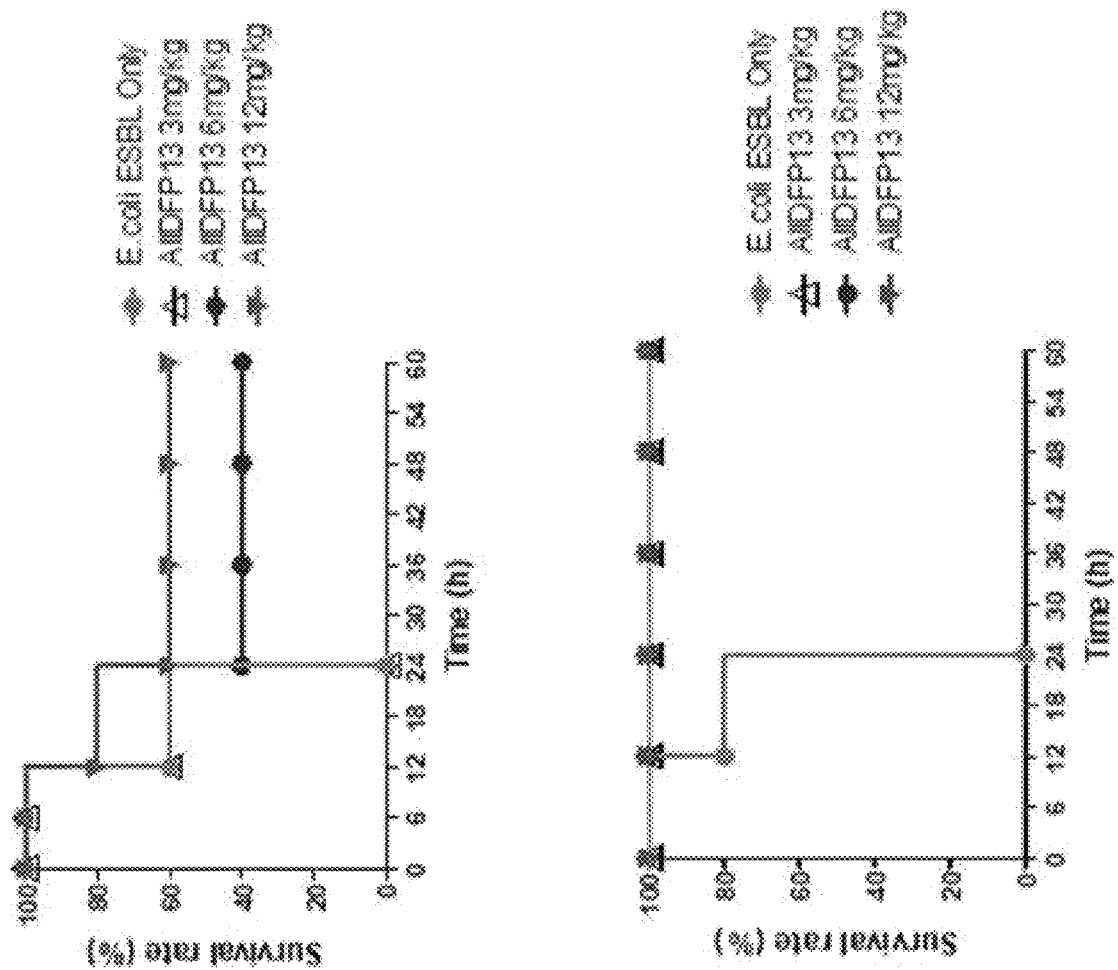
Figure 5B:
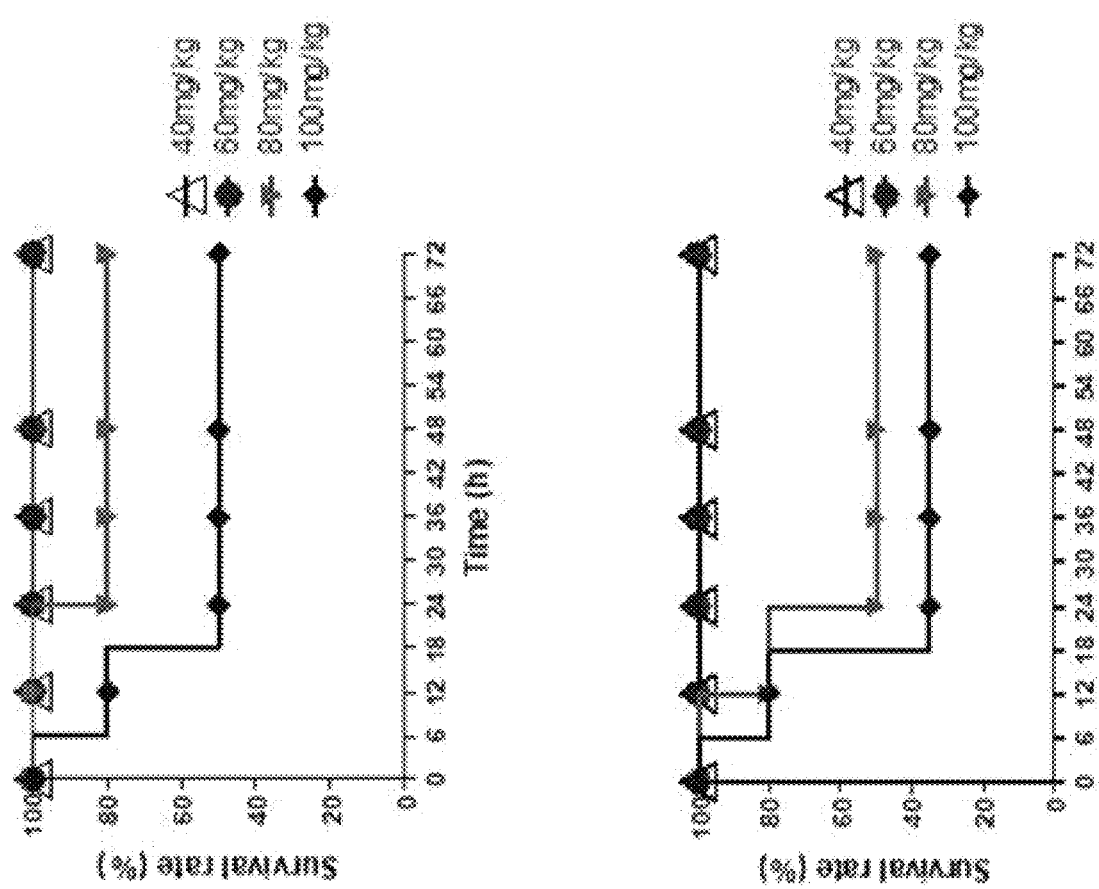
Figure 5C:
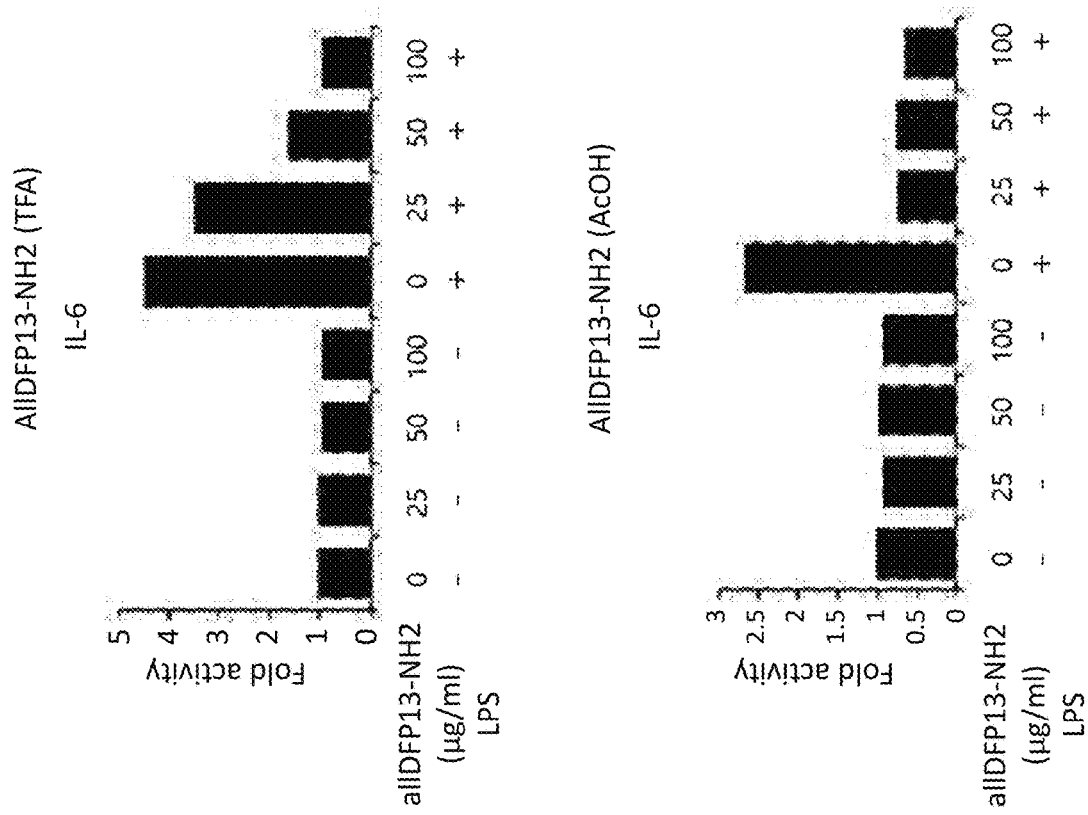

FIGS. 5A to 5C illustrate the antibiotic effect, toxic effect and antiinflammatory cytokine-inhibitory effect of the allD FP13-NH$_2$ (AcOH) peptide according to Example 9 of the present invention:

FIG. 5A shows the comparison of the antibiotic effects between AllD FP13-NH$_2$ (TFA)(top) and AllD FP13-NH$_2$ (AcOH)(bottom) against *Escherichia coli* (ESBL);

FIG. 5B shows the comparison of in vivo toxicity between AllD FP13-NH$_2$ (TFA)(top) and AllD FP13-NH$_2$ (AcOH)(bottom); and FIG. 5C shows the comparison of anti-inflammatory cytokine (IL-6)-inhibitory effects between AllD FP13-NH$_2$ (TFA; top) and AllD FP13-NH$_2$ (AcOH; bottom).

Figure 6:
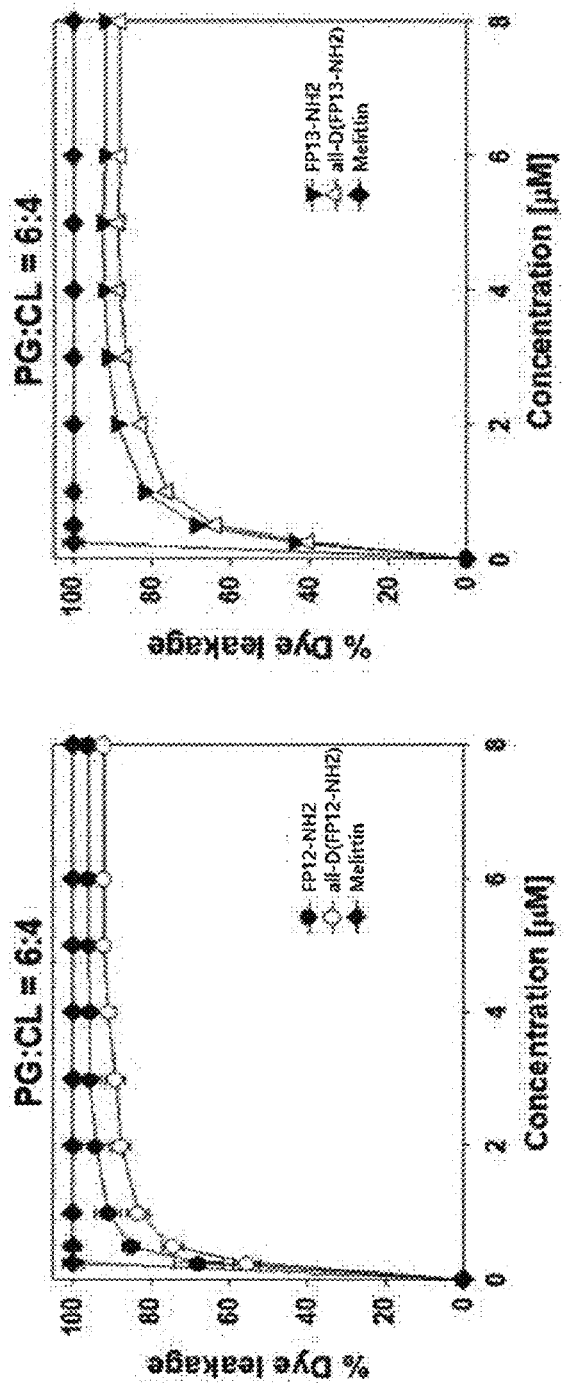

FIG. 6 is a set of graphs showing the result of measuring the disruption ability of peptides with respect to liposomes mimicking the cell membranes of gram-positive bacteria of embodiment 11 of the present invention.

MODES OF THE INVENTION

The present invention provides a polypeptide represented by the general sequence formula as follows:

Ln-X1-L-X2-V-X3-X4-X5-R-X6-L-X7 (SEQ ID NO:19)     [General Formula]

In the general formula,
n is 0 or 1;
L is leucine;
V is valine;
R is arginine;
X1 is lysine (K) or arginine (R);
X2 is glycine (G) or arginine (R);
X3 is glutamic acid (E) or lysine (K);
X4 is alanine (A) or leucine (L);
X5 is lysine (K) or arginine (R);
X6 is tyrosine (Y), alanine (A), tryptophan (W), lysine (K) or aspartic acid (D); and
X7 is aspartic acid (D) or arginine (R),
however, a polypeptide having an amino acid sequence of K-L-G-V-E-A-K-R-Y-L-D (SEQ ID NO:1) is excluded.

In one embodiment of the present invention, one or more polypeptides of 9 types of the polypeptides represented by the general formula 1) to 9) as follows:

1) a polypeptide represented by the general formula, in which
n is 0;
X1 is lysine (K);
X2 is glycine (G);
X3 is glutamic acid (E);
X4 is alanine (A);
X5 is lysine (K);
X6 is tyrosine (Y), and
X7 is arginine (R),
that is, a polypeptide having an amino acid sequence of KLGVEAKRYLR (SEQ ID NO: 2);

2) a polypeptide represented by the general formula, in which
n is 1;
X1 is arginine (R);
X2 is glycine (G);
X3 is glutamic acid (E);
X4 is alanine (A);
X5 is lysine (K);
X6 is tyrosine (Y), and
X7 is arginine (R),
that is, a polypeptide having an amino acid sequence of LRLGVEAKRYLR (SEQ ID NO: 3);

3) a polypeptide represented by the general formula, in which
n is 1;
X1 is arginine (R);
X2 is glycine (G);
X3 is glutamic acid (E);
X4 is leucine (L);
X5 is lysine (K);
X6 is tyrosine (Y), and
X7 is arginine (R),
that is, a polypeptide having an amino acid sequence of LRLGVELKRYLR (SEQ ID NO: 4);

4) a polypeptide represented by the general formula, in which
n is 0;
X1 is lysine (K);
X2 is glycine (G);
X3 is glutamic acid (E);
X4 is alanine (A);
X5 is leucine (L);
X6 is tyrosine (Y), and
X7 is aspartic acid (D),
that is, a polypeptide having an amino acid sequence of KLGVEALRYLD (SEQ ID NO: 5);

5) a polypeptide represented by the general formula, in which
n is 0;
X1 is arginine (R);
X2 is arginine (R);
X3 is lysine (K);
X4 is leucine (L);
X5 is arginine (R);
X6 is tyrosine (Y), and
X7 is arginine (R), that is, a polypeptide having an amino acid sequence of RLRVKLRRYLR (SEQ ID NO: 15);
6) a polypeptide represented by the general formula, in which
n is 0;
X1 is lysine (K);
X2 is arginine (R);
X3 is lysine (K);
X4 is leucine (L);
X5 is arginine (R);
X6 is tyrosine (Y), and
X7 is arginine (R),
that is, a polypeptide having an amino acid sequence of KLRVKLRRYLR (SEQ ID NO: 16);
7) a polypeptide represented by the general formula, in which
n is 0;
X1 is lysine (K);
X2 is arginine (R);
X3 is lysine (K);
X4 is leucine (L);
X5 is arginine (R);
X6 is alanine (A), and
X7 is arginine (R),
that is, a polypeptide having an amino acid sequence of KLRVKLRRALR (SEQ ID NO: 10);
8) a polypeptide represented by the general formula, in which
n is 0;
X1 is lysine (K);
X2 is arginine (R);
X3 is lysine (K);
X4 is leucine (L);
X5 is arginine (R);
X6 is tryptophan (W), and
X7 is arginine (R),
that is, a polypeptide having an amino acid sequence of KLRVKLRRWLR (SEQ ID NO: 11); and
9) a polypeptide represented by the general formula, in which
n is 0;
X1 is lysine (K);
X2 is arginine (R);
X3 is lysine (K);
X4 is leucine (L);
X5 is arginine (R);
X6 is lysine (K), and
X7 is arginine (R),
that is, a polypeptide having an amino acid sequence of KLRVKLRRKLR (SEQ ID NO: 12).

The term "polypeptide" used herein refers to a linear molecule formed by connecting amino acid residues by peptide bonds. The polypeptide of the present invention may be prepared by a chemical synthesis method known in the art (e.g., solid-phase synthesis techniques) as well as a molecular biology method (Merrifield, *J. Amer. Chem. Soc.* 85: 2149-54(1963); Stewart, et al., Solid Phase Peptide Synthesis, 2nd. ed., Pierce Chem. Co.: Rockford, 111(1984)).

In addition, in the range of the polypeptide of the present invention, a biologically functional equivalent having a variation in an amino acid sequence exhibiting equivalent biological activity to the polypeptide of the present invention may be included. The variation in an amino acid sequence may be generated based on the relative similarity, for example, hydrophobicity, hydrophilicity, a charge or a size, of an amino acid substituent. Through analyses on the size, shape and type of an amino acid side chain substituent, it can be seen that all of arginine, lysine and histidine are positively-charged residues; alanine, glycine and serine have similar sizes; and phenylalanine, tryptophan and tyrosine have similar shapes. Therefore, based on these considerations, the arginine, lysine and histidine; the alanine, glycine and serine; or the phenylalanine, tryptophan and tyrosine may be biologically functional equivalents.

For introduction of the variation, a hydrophobicity index of amino acids may be considered. A hydrophobicity index is assigned to each amino acid according to hydrophobicity and a charge. In addition, it is also known that substitution between amino acids having similar hydrophilicity result in peptides having equivalent biological activity.

Amino acid exchange in peptides that do not entirely change molecular activity is known in the art (H. Neurath, R. L. Hill, The Proteins, Academic Press, New York, 1979). The most generally occurring exchange is the exchange between amino acid residues, for example, Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Considering the variations with the above-described biologically equivalent activity, the polypeptide of the present invention is construed to include a sequence exhibiting substantial identity with a sequence listed in the accompanying sequence listing. The substantial identity may refer to a sequence exhibiting at least 80%, 90% or 95% homology when any different sequence is aligned as much as possible with the sequence of the present invention and is analyzed using an algorithm conventionally used in the art. An alignment method for sequence comparison is known in the art (Huang et al., *Comp. Appl. BioSci.* 8:155-65(1992); Pearson et al., *Meth. Mol. Biol.* 24:307-31(1994)).

In addition, in one embodiment of the present invention, the polypeptide represented by the general sequence formula according to the present invention may be a peptidomimetic including an L-type peptide, a D-type peptide and a peptoid, or non-natural amino acids.

The D-type polypeptide is an enantiomer which has the same amino acid sequence as the L-type polypeptide, and refers to an allomeric type polypeptide.

In an exemplary embodiment of the present invention, for example, as an allomeric type polypeptide which has the same amino acid sequence as FP12-NH$_2$ (SEQ ID NO: 6), allD FP12-NH$_2$ (SEQ ID NO: 8) is provided.

The term "allD" used to name a polypeptide herein refers to a D-type polypeptide.

The polypeptide, which is a peptidomimetic including the L-type, D-type and a peptoid, or non-natural amino acids, may be prepared by various methods known in the art according to a predetermined amino acid sequence.

In one embodiment of the present invention, an end of the polypeptide represented by the general sequence formula according to the present invention is alkylated, PEGylated, or amidated.

In an exemplary embodiment of the present invention, in the polypeptide according to the present invention, the N terminus of allD FP13-NH$_2$ (AcOH) (SEQ ID NO: 13) was PEGylated, thereby providing PEG-allD FP13-NH$_2$ (AcOH) (SEQ ID NO: 14). For PEGylation, the polypeptide according to the present invention may react with Fmoc-NH-PEG2-CH$_2$COOH, but the present invention is not limited thereto. Here, the molecular weight (MW) of polyethylene glycol is 385.4 Da.

Conditions for PEGylation may be adjusted by those of ordinary skill in the art according to the selected polypeptide, and PEGylation may be performed by various methods known in the art.

Conditions for alkylation or amidation may also be adjusted by those of ordinary skill in the art depending on the selected polypeptide, and the alkylation or amidation may be performed by various methods known in the art.

In one embodiment of the present invention, an amine group ($NH_2$) may be added to the C terminus of the polypeptide represented by the general sequence formula according to the present invention.

In an exemplary embodiment of the present invention, as the polypeptide to which an amine group ($NH_2$) is added to the C terminus of FP12 (SEQ ID NO: 15) in the polypeptide according to the present invention, FP12-$NH_2$ (SEQ ID NO: 6) is provided.

The term "—$NH_2$" used to name a polypeptide herein refers to the C terminus of the polypeptide to which an amine group ($NH_2$) is added.

The addition of an amine group ($NH_2$) to the C terminus of the polypeptide may be performed by various methods known in the art.

In addition, in the range of the polypeptide of the present invention, a pharmaceutically acceptable salt thereof may also be included.

The term "pharmaceutically acceptable" used herein refers to a peptide which is suitable to be used in contact with tissue of a subject (e.g., a human) due to a reasonable benefit/risk ratio without excessive toxicity, stimulus, allergic response or other problems or complications, and is included in the scope of sound medical judgment. The pharmaceutically acceptable salt includes, for example, an acid addition salt formed by a pharmaceutically acceptable free acid and a pharmaceutically acceptable metal salt.

Examples of suitable acids may include hydrochloric acid, bromic acid, sulfuric acid, nitric acid, perchloric acid, fumaric acid, maleic acid, phosphoric acid, glycolic acid, lactic acid, salicylic acid, succinic acid, p-toluenesulfonic acid, tartaric acid, acetic acid, citric acid, methanesulfonic acid, formic acid, benzoic acid, malonic acid, gluconic acid, naphthalene-2-sulfonic acid, and benzenesulfonic acid. The acid addition salt may be prepared by a conventional method, for example, by dissolving a compound in an excessive amount of acid aqueous solution, and precipitating the salt using a water-miscible organic solvent such as methanol, ethanol, acetone or acetonitrile. In addition, the acid addition salt may be prepared by heating equimolar amounts of compound and an acid or alcohol in water, and evaporating and then drying the mixture, or suction filtering the precipitated salt.

Salts induced from suitable bases may include alkali metals such as sodium and potassium, alkaline earth metals such as magnesium, and ammonium, but the present invention is not limited thereto. The alkali metals or alkaline earth metals may be obtained by, for example, dissolving a compound in an excessive alkali metal hydroxide or alkaline earth metal hydroxide solution, filtering an undissolved compound salt, and evaporating and drying the filtrate. Here, it is pharmaceutically suitable that a metal salt, particularly, a sodium, potassium or calcium salt is prepared, and in addition, a silver salt corresponding thereto may be obtained by reacting an alkali metal or alkaline earth metal salt with a suitable silver salt (e.g., silver nitrate).

As a pharmaceutically acceptable salt of the above-described polypeptide, the present invention provides an acetate salt of the above-described polypeptide.

More specifically, an acetate salt substituent of trifluoroacetic acid (TFA) of the polypeptide according to the present invention is provided.

More specifically, the present invention provides an acetate salt of a polypeptide represented by the above-described general formula for a sequence; a polypeptide, which is a peptidomimetic including an L-type peptide, a D-type peptide and a peptoid, or non-natural amino acids; a polypeptide which end of the polypeptide is alkylated, PEGylated or amidated; or a polypeptide to which an amine group ($NH_2$) is added to the C terminus.

The term "AcOH" used to name a polypeptide herein means an acetate salt of the polypeptide.

The polypeptide according to the present invention and a salt substitution thereof have one or more characteristics as follows:

binding ability to lipopolysaccharide (LPS) of gram-negative bacteria;
selective disruption ability against bacterial cell membrane;
resistance to proteolytic enzymes;
cell membrane disruption ability against gram-positive bacteria; and
binding ability to gram-positive bacteria-derived lipoteichoic acid (LTA) or lipoprotein (LPP).

In an exemplary embodiment of the present invention, the following characteristics of the polypeptide according to the present invention and a salt substitution thereof were confirmed, but the present invention is not limited thereto.

In an exemplary embodiment of the present invention, it was confirmed that the polypeptide according to the present invention and a salt substitution thereof has a strong binding ability to lipopolysaccharide (LPS) (Example 1).

In addition, in an exemplary embodiment of the present invention, it was confirmed that the polypeptide according to the present invention and a salt substitution thereof has disruption ability against a bacterial cell membrane (Examples 6 and 11). Particularly, it did not exhibit disruption ability against the cell membrane of a red blood cell, proving safety (Example 6).

In addition, in an exemplary embodiment of the present invention, it was confirmed that the polypeptide according to the present invention and a salt substitution thereof has excellent resistance to proteolytic enzymes (Example 7). Even when treated together with a proteolytic enzyme, the polypeptide according to the present invention and a salt substitution thereof exhibits excellent antibacterial activity, confirming that stability against proteolytic enzymes is ensured.

In addition, in an exemplary embodiment of the present invention, it was confirmed that the polypeptide according to the present invention and a salt substitution thereof have excellent binding ability to lipoteichoic acid (LTA) and lipoprotein (LPP), which are components for the cell wall of gram-positive bacteria (Example 12).

In addition, in an exemplary embodiment of the present invention, it was confirmed that the polypeptide according to the present invention and a salt substitution thereof exhibit insignificant hemolytic activity, confirming that toxicity is very low (Example 4).

In addition, the present invention provides a composition for preventing, alleviating or treating sepsis, which includes the polypeptide represented by the general sequence formula or an acetate salt substitution of trifluoroacetic acid thereof as an active ingredient.

In addition, the present invention provides a pharmaceutical/food/health food/cosmetic/quasi-drug/feed composition for preventing, alleviating or treating sepsis, which includes the polypeptide represented by the general sequence formula or an acetate salt substitution of trifluoroacetic acid thereof as an active ingredient.

The present invention provides a method of preventing or treating sepsis, which includes administering the polypeptide represented by the general sequence formula or an acetate salt substitution of trifluoroacetic acid thereof into a subject in need thereof.

In addition, the present invention provides a use of the polypeptide represented by the general sequence formula or an acetate salt substitution of trifluoroacetic acid thereof for preventing, alleviating or treating sepsis.

Further, the present invention provides a use of the polypeptide represented by the general sequence formula or an acetate salt substitution of trifluoroacetic acid thereof for preparing a preparation for preventing, alleviating or treating sepsis.

The term "sepsis" used herein refers to a condition in which a severe inflammatory response occurs throughout the body through infection with microorganisms. When two or more symptoms among fever in which a body temperature increases to 38° C. or more, hypothermia in which a body temperature decreases to 36° C. or less, an increase in respiratory rate to 24 beats per minute (tachypnea), an increase in heart rate to 90 beats per minute (tachycardia), or an increase or significant decrease in the number of white blood cells are observed by a blood test, it is called systemic inflammatory response syndrome (SIRS). When SIRS is caused by a microbial infection, it is called sepsis. Pathogens continuously or intermittently enter the bloodstream from infectious lesions of the body, and settle in various organ tissues, thereby forming lesions, and showing severe systemic symptoms. Causative bacteria include *Staphylococcus, Streptococcus, Escherichia, Pseudomonas aeruginosa, Mycobacterium tuberculosis, Klebsiella pneumoniae*, fungi, and anaerobes, but the present invention is not limited thereto.

In addition, the present invention provides an antibacterial composition, which includes the polypeptide represented by the general sequence formula or an acetate salt substitution of trifluoroacetic acid thereof as an active ingredient.

In addition, the present invention provides an antibacterial pharmaceutical/food/health food/cosmetic/quasi-drug/feed composition, which includes the polypeptide represented by the general sequence formula or an acetate salt substitution of trifluoroacetic acid thereof as an active ingredient.

The present invention provides an antibacterial method which includes administering the polypeptide represented by the general sequence formula or an acetate salt substitution of trifluoroacetic acid thereof into a subject in need thereof.

In addition, the present invention provides an antibacterial use of the polypeptide represented by the general sequence formula or an acetate salt substitution of trifluoroacetic acid thereof.

Further, the present invention provides a use of the polypeptide represented by the general sequence formula or an acetate salt substitution of trifluoroacetic acid thereof for preparing an antibacterial agent.

The term "antibacterial" or "antibacterial activity" used herein refers to a characteristic of resistance against microorganisms such as bacteria or fungi, and more particularly, a characteristic of inhibiting the growth or proliferation of bacterial by an antibiotic material.

The term "antibacterial composition" used herein is a composition having activity of suppressing the growth of microorganisms such as bacteria or fungi, and may include all types used in various fields requiring an antibacterial effect, for example, medicine, a cosmetic, a quasi-drug, a food additive or a feed additive. Specifically, such a composition may be used as an antibiotic or antifouling agent in medicines, for the purpose of a preservative or antibacterial purpose in food, for the purpose of an antibacterial, bactericidal or antiseptic effect in agriculture, may be used in products directly related to microorganisms for preventing dandruff, preventing athlete's foot, suppressing armpit odor, or anti-acne in cosmetics and household products, or used for the purpose of a preservative, antibacterial or bactericidal effect in a cleaning product or detergent for dishwashing, but the present invention is not limited thereto.

In one embodiment of the present invention, antibacterial targets of the antibacterial composition according to the present invention include gram-negative bacteria, gram-positive bacteria, antibiotic-resistant gram-negative bacteria, and antibiotic-resistant gram-positive bacteria.

The term "gram negative bacteria" used herein refers to bacteria stained red when stained by a gram staining method, and generally has strong pigment resistance and strong surfactant resistance. The gram-negative bacteria of the present invention include all types of gram-negative bacteria containing an endotoxin, for example, strains of the genus *Escherichia*, the genus *Pseudomonas*, the genus *Acinetobacter*, the genus *Salmonella*, the genus *Klebsiella*, the genus *Neisseria*, the genus *Enterobacter*, the genus *Shigella*, the genus *Moraxella*, the genus *Helicobacter*, the genus *Stenotrophomonas*, the genus *Bdellovibrio*, and the genus *Legionella*, but the present invention is not limited thereto. Specifically, the gram-negative bacteria include, but is not limited to, *Escherichia coli, Pseudomonas aeruginosa, Pseudomonas fluorescens, Pseudomonas putida, Pseudomonas chlororaphis, Pseudomonas pertucinogena, Pseudomonas stutzeri, Pseudomonas syringae, Acinetobacter baumannii, Acinetobacter lwoffii, Acinetobacter calcoaceticus, Acinetobacter haemolyticus, Salmonella enterica, Salmonella bongori, Salmonella enteritidis, Salmonella typhimurium, Salmonella gallinarum, Salmonella pullorum, Salmonella mbandaka, Salmonella choleraesuis, Salmonella thompson, Salmonella infantis, Salmonella derby, Klebsiella pneumoniae, Klebsiella granulomatis, Klebsiella oxytoca, Klebsiella terrigena, Neisseria gonorrhoeae, Neisseria meningitidis, Enterobacter aerogenes, Enterobacter cloacae, Shigella boydii, Shigella dysenteriae, Shigella flexneri, Shigella sonnei, Moraxella catarrhalis, Moraxella lacunata, Moraxella bovis, Helicobacter pylori, Helicobacter heilmannii, Helicobacter felis, Helicobacter mustelae, Helicobacter fenelliae, Helicobacter rappini, Helicobacter hepaticus, Helicobacter bilis, Helicobacter pullorum, Stenotrophomonas maltophilia, Stenotrophomonas nitritireducens, Bdellovibrio bacteriovorus, Legionella pneumophila, Legionella anisa, Legionella birminghamensis, Legionella bozemanii, Legionella cincinnatiensis, Legionella dumoffii, Legionella feeleii, Legionella gormanii, Legionella hackelia, Legionella israelensis, Legionella jordanis, Legionella lansingensis, Legionella longbeachae, Legionella longbeachae, Legionella micdadei, Legionella oakridgensis, Legionella sainthelensi, Legionella tucsonensis*, and *Legionella wadsworthii*.

The term "gram positive bacteria" used herein refers to bacteria which are stained royal blue or purple through gram staining, and may include strains of the genus *Staphylococcus*, the genus *Enterococcus*, the genus *Streptococcus*, and the genus *Clostridium*, but the present invention is not limited thereto. Specifically, the gram-positive bacteria include *Staphylococcus aureus, Staphylococcus epidermidis, Enterococcus faecium, Streptococcus pneumoniae,* and *Bacillus anthracis*, but the present invention is not limited thereto.

The term "antibiotic-resistant gram-positive bacteria" used herein includes, for example, methicillin-resistant gram-positive bacteria, carbapenem-resistant gram-positive bacteria, vancomycin-resistant gram-positive bacteria, macrolide and multidrug-resistant gram-positive bacteria, but the present invention is not limited thereto.

The "antibiotic-resistant gram-negative bacteria" used herein include, for example, streptomycin-resistant gram-negative bacteria, colistin-resistant gram-negative bacteria, carbapenem-resistant gram-negative bacteria, chloramphenicol-resistant gram-negative bacteria, tetracyclines-resistant gram-negative bacteria, cefotaxime-resistant gram-negative bacteria, imipenem-resistant gram-negative bacteria, ESBL-resistant gram-negative bacteria, tigecycline-resistant gram-negative bacteria and multidrug-resistant gram-negative bacteria, but the present invention is not limited thereto.

In one embodiment of the present invention, bacteria targeted by the antibacterial composition may be one or more selected from the group consisting of *Escherichia coli* DH5α, *Escherichia coli* K1, *Acinetobacter baumannii, Pseudomonas aeruginosa, Salmonella enteritidis, Salmonella typhimurium, Klebsiella pneumoniae, Staphylococcus aureus* and *Staphylococcus epidermidis*.

In addition, in one embodiment of the present invention, the bacteria targeted by the antibacterial composition may be one or more antibiotic-resistant bacteria selected from the group consisting of ESBL-resistant bacteria, carbapenem-resistant bacteria and colistin-resistant bacteria. For example, the antibiotic-resistant bacteria may be ESBL (*E. coli*), carbapenem resistant (CR)-*Acinetobactor baumannii*, CR-*Klebsiella pneumoniae*, CR-*Pseudomonas aeruginosa*, and colistin-resistant *Acinetobactor baumannii*, but the present invention is not limited thereto.

In addition, the present invention provides a composition for preventing, alleviating or treating an infectious disease, which includes the polypeptide represented by the general sequence formula or an acetate salt substitution of trifluoroacetic acid thereof as an active ingredient.

In addition, the present invention provides a pharmaceutical/food/health food/cosmetic/quasi-drug/feed composition for preventing, alleviating or treating an infectious disease, which includes the polypeptide represented by the general sequence formula or an acetate salt substitution of trifluoroacetic acid thereof as an active ingredient.

The present invention provides a method of preventing or treating an infectious disease, which includes administering the polypeptide represented by the general sequence formula or an acetate salt substitution of trifluoroacetic acid thereof into a subject in need thereof.

In addition, the present invention provides a use of the polypeptide represented by the general sequence formula or an acetate salt substitution of trifluoroacetic acid thereof for preventing, alleviating or treating an infectious disease.

Further, the present invention provides a use of the polypeptide represented by the general sequence formula or an acetate salt substitution of trifluoroacetic acid thereof for preparing a preparation for preventing, alleviating or treating an infectious disease.

The term "infectious disease" used herein refers to a disease caused by disease-causing pathogens such as viruses, bacteria, fungi, and parasites, which spread to or invade animals or humans, and for the purpose of the present invention, the infectious disease means all types of infectious disease caused by gram-negative bacteria or gram-positive bacteria.

For example, the infectious disease includes infectious diseases caused by gram-negative bacteria, such as pneumonia, peritonitis, meningitis, wound infection, osteoarthritis, cholecystitis, urinary tract infection, endocarditis, myocarditis, pericarditis, arthritis, pharyngitis, gonorrhea, bacterial dysentery, enteritis, conjunctivitis, gastritis, otitis media, cystitis, and lymphangitis, but the present invention is not limited thereto.

For example, the infectious disease includes infectious diseases caused by gram-positive bacteria, such as laryngopharyngitis, impetigo, rheumatic fever, glomerulonephritis, neonatal sepsis, meningitis, pharyngitis, pneumonia, endocarditis, scarlet fever, SSTI (skin and soft tissue infection), deep soft tissue infection, empyema, and vaginitis, but the present invention is not limited thereto.

The pharmaceutical composition of the present invention may further include suitable carrier, excipient and diluent, which are conventionally used in preparation of a pharmaceutical composition. The pharmaceutical composition according to the present invention may be used in an oral formulation such as a powder, a granule, a tablet, a capsule, a suspension, an emulsion, a syrup, or an aerosol, an external preparation, a suppository, or a sterilized injectable solution according to a conventional method.

Examples of carriers, excipients and diluents that can be included in the pharmaceutical composition of the present invention may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

The pharmaceutical composition of the present invention may be formulated with a diluent or an excipient such as a filler, a bulking agent, a binder, a wetting agent, a disintegrant, a surfactant, which are conventionally used. A solid formulation for oral administration may be a tablet, pill, powder, granules or a capsule, and such a solid formulation may be prepared by mixing at least one of excipients, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a oral liquids, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration may be a sterilized aqueous solution, a non-aqueous solvent, a suspension, an emulsion, a lyophilized product or a suppository. As the non-aqueous solvent or suspension, propylene glycol, polyethylene glycol, a vegetable oil such as olive oil, or an injectable ester such as ethyl oleate may be used. As a suppository base, Witepsol, macrogol, Tween 61, cacao butter, laurinum, or glycerogelatin may be used.

The term "prevention" used herein refers to all actions of preventing, inhibiting or delaying symptoms generated by a disease by administration of the composition according to the present invention.

The term "treatment" or "alleviation" used herein refers to all actions involved in improving or beneficially changing symptoms by administration of the composition according to the present invention.

The term "administration" used herein refers to the provision of the composition of the present invention to a subject by a suitable method.

The term "subject" used herein refers to a target in need of prevention or treatment. For example, the subject may be a mammal such as a human or a non-human primate, a mouse, a dog, a cat, a horse, a sheep, or a cow.

The composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. Specifically, the pharmaceutical composition may be administered at a dose of 0.001 to 1,000 mg/kg, 0.01 to 100 mg/kg, 0.01 to 10 mg/kg, 0.1 to 10 mg/kg or 0.1 to 1 mg/kg once or in divided portions a day. In consideration of all of the above-mentioned parameters, it is important to achieve the maximum effect with the minimum dose without a side effect, and such a dose may be determined by one of ordinary skill in the art. Specifically, the effective amount of the pharmaceutical composition according to the present invention may be determined according to a patient's age, sex, condition, body weight, an absorption rate of the active ingredient in the body, an inactivation rate, an excretion rate, a type of disease, or a concomitant drug.

The pharmaceutical composition of the present invention may be administered into a subject via various routes. All administration routes may be expected, and the pharmaceutical composition of the present invention may be administered by, for example, orally, or intrarectal, intravenous, intramuscular, subcutaneous, intrauterine, intradural or intracerebrovascular injection.

The pharmaceutical composition according to the present invention may further include one or more known materials effective in alleviating, preventing or treating sepsis or septic shock; preventing bacterial infection; and alleviating, preventing or treating an infectious disease.

The pharmaceutical composition of the present invention may further include a bronchodilator, an antihistamine, or an anti-inflammatory analgesic drug in addition to the active ingredient.

For example, the bronchodilator may be a 3 agonist, an anticholinergic agent, or methylxanthine, the antihistamine may be acrivastine, cetirizine, desloratadine, fexofenadine, levocetirizine, loratadine, mizolastine, alimemazine, chlocertirizine, clemastine, cyproheptadine, hydroxyzine, ketotifen or promethazine, and the anti-inflammatory analgesic drug may be aspirin, diclofenac, fenoprofen, flurbiprofen, ibuprofen, indomethacin, ketoprofen, naproxen, piroxicam, sulindac, celecoxib, valdecoxib, or rofecoxib.

In an exemplary embodiment of the present invention, it was confirmed that the polypeptide according to the present invention and a salt thereof have a high binding ability to LPS by measuring the binding ability of the polypeptide according to the present invention and a salt thereof with LPS (Example 1).

In addition, in an exemplary embodiment of the present invention, it was confirmed that the polypeptide according to the present invention and a salt thereof exhibit excellent antibacterial activity (Examples 2, 3 and 10).

In addition, in an exemplary embodiment of the present invention, it was confirmed that the polypeptide according to the present invention and a salt thereof exhibit a strong antibiotic effect (Examples 8 and 9).

In addition, the present invention provides a polynucleotide encoding the polypeptide.

The term "polynucleotide" is a polymer of deoxyribonucleotides or ribonucleotides, which are present in single or double strand(s). The polynucleotide encompasses an RNA genome sequence, DNA (gDNA and cDNA) and an RNA sequence transcribed therefrom, and includes an analog of a natural polynucleotide unless otherwise specified.

The polynucleotide includes the nucleotide sequence, and also includes a sequence complementary thereto. The complementary sequence includes not only a perfectly complementary sequence, but also a substantially complementary sequence. it refers to a sequence capable of hybridizing with the nucleotide sequence under stringent conditions known in the art.

In addition, the polynucleotide may be modified. The modification includes addition, deletion, non-conservative substitution or conservative substitution of a nucleotide. The polynucleotide encoding the amino acid sequence is interpreted to also include a nucleotide sequence exhibiting substantial identity to the nucleotide sequence. The substantial identity may be a sequence having at least 80%, 90% or 95% homology when the nucleotide sequence is aligned to any different sequence such that they correspond to be maximal correspondence, and the aligned sequence is analyzed using an algorithm conventionally used in the art.

In addition, the present invention provides a recombinant vector including the polynucleotide.

The term "vector" used herein refers to a means for expressing a target gene in host cells. For example, the vector includes a plasmid vector, a cosmid vector, a bacteriophage vector, and viral vectors such as an adenovirus vector, a retrovirus vector and an adeno-associated virus vector. A vector that can be used as the recombinant vector may be constructed by manipulating a plasmid often used in the art (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series or pUC19), a phage (e.g., λ λ λ λ Δ or M13) or a virus (e.g., CMV or SV40).

In the recombinant vector, a polynucleotide encoding the peptide may be operatively linked to a promoter. The term "operatively linked" used herein means a function linkage between a nucleotide expression regulatory sequence (e.g., promoter sequence) and a different nucleotide sequence. Therefore, the regulatory sequence may regulate the transcription and/or translation of the different nucleotide sequence.

The recombinant vector may typically be constructed as a vector for cloning or expression. The expression vector may be a conventional vector used to express a foreign protein in a plant, animal or microorganism in the art. The recombinant vector may be constructed through various methods known in the art.

In addition, the present invention provides a host cell transformed by the recombinant vector.

As the host cell, any host cell known in the art may be used, and prokaryotic cells, for example, strains of the family Enterobacteriaceae including *E. coli* JM109, *E. coli* BL21, *E. coli* RR1, *E. coli* LE392, *E. coli* B, *E. coli* X 1776, or *E. coli* W3110, a strain of the genus *Bacillus* such as *Bacillus subtilis* or *Bacillus thuringiensis, Salmonella typhimurium, Serratia marcescens*, and various *Pseudomonas* species may be used, and when transformed into eukaryotic cells, as host cells, yeast cells (*Saccharomyces cerevisiae*), insect cells, plant cells and animal cells, for example, SP2/0, Chinese hamster ovary (CHO) K1, CHO DG44, PER.C6, W138, BHK, COS-7, 293, HepG2, Huh7, 3T3, RIN and MDCK cell lines may be used.

The present invention provides a method of preparing a polypeptide represented by the general sequence formula according to the present invention, which includes culturing the host cells.

The insertion of the polynucleotide or a recombinant vector including the same into host cells may be used by an insertion method widely known in the art. The delivery method may be, for example, a $CaCl_2$) method or an electroporation method when the host cell is a prokaryotic cell, and microinjection, calcium phosphate, precipitation, liposome-mediated transfection and gene bombardment when the host cell is a eukaryotic cell, but the present invention is not limited thereto.

The method of selecting the transformed host cells may be easily carried out by a method widely known in the art using a phenotype expressed by a selection marker. For example, when the selection marker is a specific antibiotic-resistant gene, a transformant is cultured in a medium containing the antibiotic so that the transformant may be easily selected.

Hereinafter, to help in understanding the present invention, exemplary examples will be suggested. However, the following examples are merely provided to more easily understand the present invention, and not to limit the present invention.

Example 1: Measurement of LPS Binding Ability of ADK-Derived Peptide Candidates for *E. coli* K1

FPT (ADK 44-54) is denoted by wild type (WT), and peptides in which a point mutation occurred at various sites in WT were manufactured (FP3, FP5, FP6, and FP9). To increase the interaction with LPS in a residue sequence of FP3, peptides were designed based on FP3- and LPS-binding models (FP12-$NH_2$ and FP13-$NH_2$), and peptides were designed by additionally introducing a non-natural amino acid and an amino acid isomer (allomeric D-type amino acid) (allD FP12-$NH_2$, allD FP13-$NH_2$, allD FP-13-9a, allD FP-13-9w, allD FP-13-9k, and allD FP13-$NH_2$ (AcOH)). In addition, an N-terminus PEGylated peptide (PEG-allD FP13-$NH_2$ (AcOH)) was additionally designed, synthesized, and provided by ANYGEN, Co. Ltd. The binding affinity between each of the provided peptides and lipopolysaccharide (LPS) was confirmed through measuring the binding affinity (Kd) using Isothermal Titration Calorimeter (ITC).

Specifically, a method of analyzing binding affinity (Kd) between a peptide and LPS is as follows.

Measurement was carried out using a Malvern MicroCal PEAQ-ITC cell instrument, and the following pretreatment was carried out to confirm interaction with LPS. The amount and morphology of a sample cell are 300 μL and coin-shaped, fixed-in-place, respectively; a syringe rotation rate was 1,200 rpm; and a temperature was 30° C., 35° C. or 25° C.

Before the experiment, LPS and the peptide were previously diluted with PBS, thereby preparing 2 mM LPS and 0.2 mM peptide. 300 μL of the peptide was added into cells in the ITC instrument, which had been washed, and 40 μL of LPS was put into a syringe. After measurement conditions for ITC (temperature, number of injections) were set, the syringe was inserted into the cell, and ITC measurement was started. When the measurement was completed, analysis is performed, and the Kd values of LPS and the peptide were calculated.

As a result of measurement, it was confirmed that all types of peptides of FP3, FP5, FP6, FP9, FP12-$NH_2$, FP13-$NH_2$, allD FP12-$NH_2$, allD FP13-$NH_2$, allD FP-13-9a, allD FP-13-9w, allD FP-13-9k, and allD FP13-$NH_2$ (AcOH) have strong LPS binding affinity, which is equal to or higher than that of FP1 (wild type, WT).

TABLE 1

| Sequence ID No. | Peptide | Sequence | Kd (calculated by ITC) |
|---|---|---|---|
| 1 | FP1(WT) | KLGVEAKRYLD | $2.38 \times 10^{-4}$ |
| 2 | FP3 | KLGVEAKRYLR | $3.32 \times 10^{-4}$ |
| 3 | FP5 | LRLGVEAKRYLR | $8.54 \times 10^{-4}$ |
| 4 | FP6 | LRLGVELKRYLR | $1.11 \times 10^{-5}$ |
| 5 | FP9 | KLGVEALRYLD | $3.26 \times 10^{-4}$ |
| 6 | FP12-NH2 | RLRVKLRRYLR-NH2 | $2.42 \times 10^{-7}$ |
| 7 | FP13-NH2 | KLRVKLRRYLR-NH2 | $1.18 \times 10^{-4}$ |
| 8 | allD FP12-NH2 | RLRVKLRRYLR-NH2 (all d-form) | $2.66 \times 10^{-5}$ |
| 9 | allD FP13-NH2 | KLRVKLRRYLR-NH2 (all d-form) | $4.78 \times 10^{-6}$ |
| 10 | allD FP-13-9a-NH2 | klrvklrralr-NH2 (all d-form) | $9.54 \times 10^{-6}$ |
| 11 | allD FP-13-9w-NH2 | klrvklrrdlr-NH2 (all d-form) | $1.74 \times 10^{-5}$ |

TABLE 1-continued

| Sequence ID No. | Peptide | Sequence | Kd (calculated by ITC) |
|---|---|---|---|
| 12 | allD FP-13-9k-NH2 | klrvklrrklr-NH2 (all d-form) | $1.99 \times 10^{-6}$ |
| 13 | allD FP13-NH2 (AcOH) | KLRVKLRRYLR-NH2 (all d-form) | $1.95 \times 10^{-5}$ |

TABLE 2

| Sequence ID No. | Peptide | Sequence | Kd (calculated by ITC) |
|---|---|---|---|
| 1 | FP1(WT) | KLGVEAKRYLD | $2.38 \times 10^{-4}$ |
| 14 | PEG-allD FP13-NH2 (AcOH) | PEG-KLRVKLRRYLR-NH2 (all d-form) PEG: Fmoc-NH-PEG | $1.75 \times 10^{-5}$ |

(In Tables 1 and 2, allD indicates a D-type amino acid)
(In Tables 1 and 2, (AcOH) indicates a salt substitution in which trifluoroacetic acid (TFA) at a terminus of the $9^{th}$ amino acid from the N terminus of a peptide is substituted with an acetate salt.)
(In Table 2, PEG indicates PEGylation. Information on peptide N-terminus PEGylation: polyethylene glycol (PEG), molecular weight (Mw)=385.4 Da, Fmoc-NH-PEG2-CH$_2$COOH)

Example 2: Evaluation of Comparison in Antibacterial Activity of allD FP13-NH$_2$ and Four Commercially Available Antibiotics Against Gram-Positive/Negative Standard Strains The antibacterial activity of one peptide (allD FP13-NH$_2$) that had been confirmed to have strong affinity for LPS among the peptides designed in Example 1 and four commercially available antibiotics against gram-positive/negative standard strains was compared.

To compare the antibacterial activity between the four commercially available antibiotics (ampicillin, gentamicin, levofloxacin and imipenem) and the allD FP13-NH$_2$ (AcOH) peptide, an antibacterial activity test was performed to measure the minimum inhibitory concentrations (MIC$_{50}$ and MIC$_{80}$) for gram-negative and gram-positive standard strains (*Escherichia coli* DH5α, *Escherichia coli* K1, *Acinetobacter baumannii*, *Pseudomonas aeruginosa*, *Salmonella enteritidis*, *Salmonella typhimurium*, and *Klebsiella pneumoniae*).

More specifically, 100 μL of a medium was dispensed into each well of a 96-well plate, and in the first column, an antibiotic and a peptide in 200 μL of the medium were dispensed. 1/2 serial dilution was performed from columns 1 to 11, and gram-negative and gram-positive bacteria which had been previously cultured were diluted (OD$_{600\ nm}$ value in dilution: approximately 0.0025) and dispensed into each well. The plate was incubated in a 37° C. incubator for 4 hours, and measured at OD$_{600\ nm}$. A bacterial growth rate was determined as 100% with the OD$_{600\ nm}$ value of a blank (well containing only medium and bacteria), and MIC$_{50}$ was determined by confirming the concentrations of the antibiotic and peptide having an OD$_{600\ nm}$ value at which a growth inhibition rate of 50% was shown, and MIC$_{80}$ was determined by confirming the concentrations (μg/ml) at which a growth inhibition rate of 80% was shown.

As a result, by comparing the allD FP13-NH$_2$ (AcOH) peptide with the four commercially available antibiotics (ampicillin, gentamicin, levofloxacin and imipenem), it was confirmed that the allD FP13-NH$_2$ (AcOH) peptide exhibits the same or superior antibacterial activity against all seven types strains of gram-positive/negative bacteria.

TABLE 3

| Organism and antimicrobial agent | MIC (μg/ml) | | |
|---|---|---|---|
| | Testing range | 50% | 80% |
| *Escherichia coli* DH (ATCC PTA-4750 | | | |
| Ampicillin | 0.125~128 | <2.0 | <4.0 |
| Gentamicin | 0.125~128 | <0.5 | <1.0 |
| Levofloxacin | 0.125~128 | <0.5 | <1.0 |
| Imipenem | 0.125~128 | <4.0 | <8.0 |
| allD-FP13-NH2 | 0.125~128 | <1.0 | <2.0 |
| *Escherichia coli* K1 | | | |
| Ampicillin | 0.125~128 | <4.0 | <8.0 |
| Gentamicin | 0.125~128 | <0.5 | <1.0 |
| Levofloxacin | 0.125~128 | <0.5 | <1.0 |
| Imipenem | 0.125~128 | <0.5 | <1.0 |
| allD-FP13-NH2 | 0.125~128 | <2.0 | <4.0 |
| *Acinetobacter baumannii* (ATCC 19606) | | | |
| Ampicillin | 0.125~128 | <32 | <64 |
| Gentamicin | 0.125~128 | <1.0 | <2.0 |
| Levofloxacin | 0.125~128 | <0.5 | <1.0 |
| Imipenem | 0.125~128 | <8.0 | <15 |
| allD-FP13-NH2 | 0.125~128 | <4.0 | <8.0 |
| *Pseudomanas aeruginosa* PAO1 (ATCC 47085D-5) | | | |
| Ampicillin | 0.125~128 | no effect | no effect |
| Gentamicin | 0.125~128 | <0.5 | <1.0 |
| Levofloxacin | 0.125~128 | <0.5 | <1.0 |

TABLE 3-continued

| Organism and antimicrobial agent | MIC (μg/ml) | | |
|---|---|---|---|
| | Testing range | 50% | 80% |
| Imipenem | 0.125~128 | <32 | <64 |
| allD-FP13-NH2 | 0.125~128 | <0.5 | <1.0 |
| *Salmonela enteritidis* (ATCC 13076) | | | |
| Ampicillin | 0.125~128 | <4.0 | <8.0 |
| Gentamicin | 0.125~128 | <0.5 | <1.0 |
| Levofloxacin | 0.125~128 | <0.5 | <1.0 |
| Imipenem | 0.125~128 | <4.0 | <8.0 |
| allD-FP13-NH2 | 0.125~128 | <1.0 | <2.0 |
| *Salmonela typhimurium* (ATCC 53648) | | | |
| Ampicillin | 0.125~128 | <1.0 | <2.0 |
| Gentamicin | 0.125~128 | <0.5 | <1.0 |
| Levofloxacin | 0.125~128 | <0.5 | <1.0 |
| Imipenem | 0.125~128 | <4.0 | <8.0 |
| allD-FP13-NH2 | 0.125~128 | <2.0 | <4.0 |
| *Klebiella pneumoniae* (ATCC 13883) | | | |
| Ampicillin | 0.125~128 | no effect | no effect |
| Gentamicin | 0.125~128 | <0.5 | <1.0 |
| Levofloxacin | 0.125~128 | <0.5 | <1.0 |
| Imipenem | 0.125~128 | <2.0 | <8.0 |
| allD-FP13-NH2 | 0.125~128 | <0.5 | <1.0 |

Example 3: Evaluation of Comparison in Antibacterial Activity of Peptides and Three Antibiotics Against Antibiotic-Resistant Bacteria (ESBL and Carbapenem-Resistant Bacteria)

To analyze the antibacterial activity of 9 types of peptides, the antibacterial activity against bacteria resistant to ampicillin (AMP), imipenem, colistin, and other five antibiotics (ESBL-*E. coli*, carbapenem resistant *A. baumannii*, carbapenem resistant *Klebsiella pneumoniae*, carbapenem resistant *Pseudomonas aeruginosa*, and colistin resistant *Acinetobactor baumannii*) was confirmed.

The antibacterial activity was evaluated according to an antibacterial activity test method for measuring the minimum inhibitory concentration 50 ($MIC_{50}$; the minimal concentration that kills 50% of bacteria).

More specifically, 100 μL of a medium was dispensed into each well of a 96-well plate, and in the first column, an antibiotic and a peptide in 200 μL of the medium were dispensed. 1/2 serial dilution was performed from columns 1 to 11 and five types of antibiotic-resistant bacteria (ESBL-resistant *E. coli*, carbapenem-resistant *A. baumannii*, carbapenem-resistant *Klebsiella pneumoniae*, carbapenem-resistant *Pseudomonas aeruginosa*, colistin-resistant *Acinetobactor baumannii*), which had been previously cultured, were diluted ($OD_{600\ nm}$ value in dilution: approximately 0.0025) and dispensed into each well. The plate was incubated in a 37° C. incubator for 4 hours, and measured at $OD_{600\ nm}$. A bacterial growth rate was determined as 100% with the $OD_{600\ nm}$ value of a blank (well containing only medium and bacteria), and a $MIC_{50}$ value was measured by confirming the concentrations of an antibiotic and a peptide which have an $OD_{600\ nm}$ value at which a growth rate of 50% was shown.

As a result, it was confirmed that the peptide according to the present invention has improved antibacterial activity compared to the three comparative antibiotics (ampicillin (AMP), imipenem and colistin). Particularly, it was confirmed that the peptide according to the present invention also has antibacterial activity against bacteria resistant to these antibiotics (particularly, a carbapenem or colistin-resistant strain).

TABLE 4

| Drugs | ESBL (*E. coli*) | Carbapenem resistant (CR)-*Acinetobactor baumannii* | CR-*Klebsiella pneumoniae* | Colistin resistant AB |
|---|---|---|---|---|
| AMP | No effect | <16 μg/ml | No effect | No effect |
| Imipenem | No effect | No effect | No effect | No effect |
| Colistin | <0.5 μg/ml | <1 μg/ml | <125 μg/ml | No effect |
| FP12 | <2 μg/ml | <16 μg/ml | <62 μg/ml | <125 μg/ml |
| FP13 | <2 μg/ml | <16 μg/ml | <62 μg/ml | <62 μg/ml |
| FP12-NH2 | <0.5 μg/ml | <4 μg/ml | <8 μg/ml | <16 μg/ml |
| FP13--NH2 | <1 μg/ml | <8 μg/ml | <16 μg/ml | <32 μg/ml |
| allD FP12-NH2 | <0.5 μg/ml | <4 μg/ml | <32 μg/ml | <16 μg/ml |
| allD FP13-NH2 | <0.5 μg/ml | <4 μg/ml | <8 μg/ml | <16 μg/ml |
| allD FP21-NH2 | <0.5 μg/ml | <1 μg/ml | <4 μg/ml | <4 μg/ml |
| allD FP13-NH2 (AcOH) | <1 μg/ml | <1 μg/ml | <32 μg/ml | <16 μg/ml |

Example 4: Measurement of Hemolytic Activity of Peptide

The following experiment was carried out to determine the toxicity of a peptide through measurement of the red blood cell hemolytic activity in a human.

The red blood cells in a human were diluted with PBS for washing, and centrifuged for 10 minutes, the washing process was repeated three times. The 8.0% red blood cell solution diluted with PBS was loaded into a 96-well microtiter plate by 100 μL and 100 μL of a peptide solution was mixed, the mixture was incubated at 37° C. for 1 hour, and then the 96-well microtiter plate was centrifuged for 5 minutes. A 100 μL of supernatant was taken and transferred to another 96-well microtiter plate, and then absorbance was measured at 405 nm. Here, a value obtained when treated with 0.1% Triton X-100 was calculated as 100% hemolysis, and the hemolytic activity of the peptide was calculated as % hemolysis by Equation 1 below.

$$\text{Cell disruption rate (\% Hemolysis)} = \frac{A-C}{B-C} \times 100 \quad \text{[Equation 1]}$$

Here, A is the absorbance at 405 nm in a peptide solution, B is the absorbance at 405 nm in a 0.1% Triton X-100, and C is the absorbance at 405 nm in a PBS solution.

Here, as a peptide for a control, melittin, which is an antibacterial peptide exhibiting strong antibacterial activity and strong hemolytic activity, was used.

Figure 1:
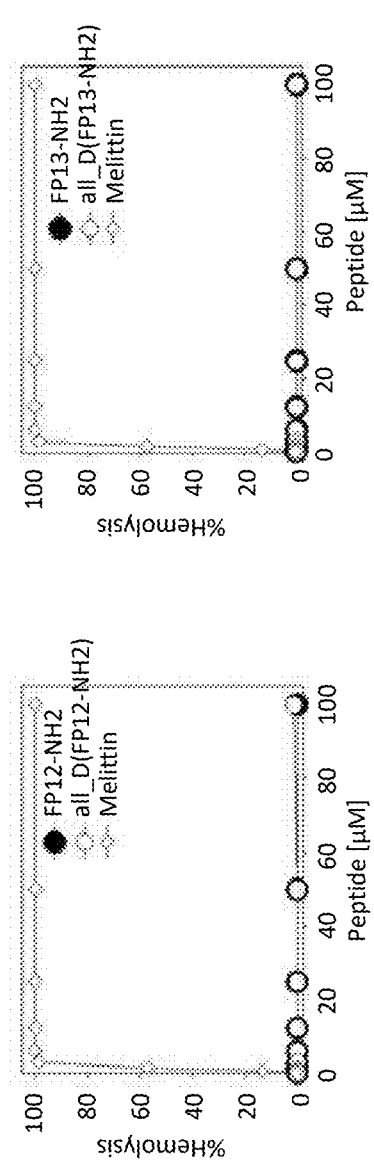
FIG. 1 is a set of graphs illustrating the result of measuring hemolytic activity according to Example 4 of the present invention.
Figure 1:
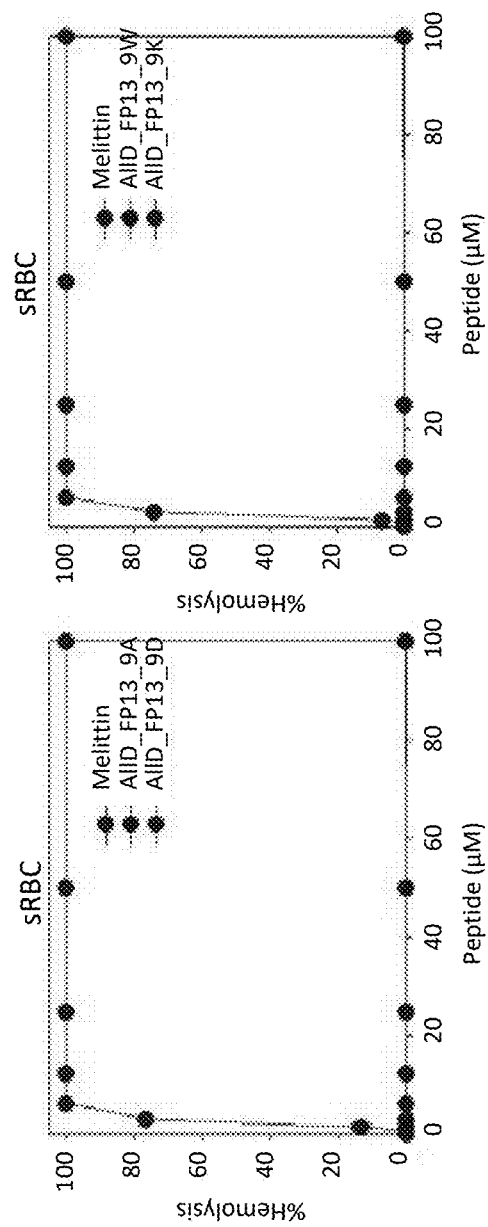

As a result, as shown in FIG. 1, it can be seen that the peptides according to the present invention exhibited almost no hemolytic activity even at a high concentration of 100 µM. On the other hand, melittin as a control showed 100% hemolytic activity even at a low concentration, indicating very high toxicity.

Example 5: Measurement of Secondary Structure of Peptide Using Circular Polarization Dichroism Spectroscopy To measure the secondary structure of the FP12-NH$_2$ and FP13-NH$_2$ peptides, an experiment was carried out as follows.

To study the secondary structure of the peptides in a biomembrane-like environment, the peptides were dissolved in a 0.3 mL solvent such that the concentration of the peptides became 100 µM per sample in an aqueous solution, 100 mM SDS, or 50 mM DPC. 1 mm path length cells were analyzed using a Jasco J-720 circular dichroism spectrophotometer, thereby obtaining an absorption value per 0.1 nm at an injection rate of 100 nm/min, and six injections were averaged, thereby obtaining a measurement value.

Circular polarization dichroism spectroscopy shows a characteristic absorption pattern depending on the secondary structure of the backbone of a polypeptide. The FP12-NH$_2$ and FP13-NH$_2$ peptides did not have a secondary structure in an aqueous solution, but had two minimal points at wavelengths of approximately 208 and 222 nm, which is the characteristic absorption pattern of an α-helix structure in DPC micelles, which is a biomembrane-like environment (FIG. 2).

From the above results, it can be predicted that these peptides will exhibit antibacterial activity while forming α-helix structures in the biomembrane of bacteria. On the other hand, it can be seen that allD (FP12-NH$_2$) and allD (FP13-NH$_2$) peptides, which were subjected to D-amino acid substitution, exactly have mirror images of a parent peptide. In contrast to the CD spectrum of the parent peptide showing a right-handed α-helix structure, the peptides have negative intensity, indicating that they have a left-handed α-helix structure (FIG. 2).

Example 6: Measurement of Disruption Ability of Peptides Against Liposomes Mimicking Gram-Negative Bacteria Cell Membrane and Red Blood Cell Membrane To study an action mechanism for FP12-NH$_2$, FP13-NH$_2$, allD FP12-NH$_2$, and allD FP13-NH$_2$ peptides, the disruption ability of the peptides against liposomes mimicking a bacterial cell membrane and a red blood cell membrane was measured.

To confirm whether the antibacterial action of the peptides exhibit the action mechanism of killing bacteria by targeting the bacterial cell membrane, liposomes encapsulating a fluorescent dye, calcein, which consist of EYPC/EYPG (7:3, w/w) mimicking the cell membrane of gram-negative bacteria and EYPC/CH (1:10, w/w) mimicking a human red blood cell were manufactured, respectively, to perform a fluorescent dye leakage assay.

EYPG is an abbreviation for egg yolk L-α-phosphatidyl-DL-glycerol, and EYPC is an abbreviation for egg yolk 1,2-diacyl-sn-glycero-3-phosphocholine. CH is an abbreviation for cholesterol. After dissolving the phospholipids composed according to the content of each component in chloroform, the chloroform was removed using a rotary evaporator, and lyophilization was performed overnight. Afterward, the dried lipid film was dissolved in a Tris-buffer solution, and calcein was dissolved in liquid nitrogen. After repeated freezing and thawing, the calcein-encapsulated liposome was manufactured using an extruder. Subsequently, after an excitation wavelength of a spectrofluorimeter (Shimadzu RF 5301 PC spectrofluorimeter, Japan) was set to 490 nm, and an emission wavelength was set to 520 nm, the peptide was administered to the liposome to measure relative dye leakage, provided that a 100% dye leakage was expressed as fluorescence intensity when 0.010% Triton-X$_{100}$ was added.

The result is shown in FIG. 3. The upper graphs of FIG. 3 show the % dye leakage for an EYPC/EYPG (7:3, w/w) liposome mimicking bacterial cells, encapsulating a fluorescent dye, calcein, by a peptide according to a peptide concentration. Here, as a control (peptide exhibiting the action mechanism of cell membrane targeting), an antibacterial peptide, melittin, was used. The lower graphs of FIG. 3 show the % dye leakage for an EYPC/CH (10:1, w/w) liposome, which is a triglyceride mimicking a human red blood, encapsulating a fluorescent dye, calcein, by a peptide according to a peptide concentration. Here, the antibacterial peptide, melittin, was used as a control (peptide exhibiting the action mechanism of cell membrane targeting).

As shown in FIG. 3, a control peptide is responsible for calcein leakage from a liposome consisting of PC/PG (7:3, w/w) mimicking a bacterial cell membrane even at a low concentration. For a PC/CH (10:1, w/w) liposome mimicking a human red blood cell, since almost 100% calcein leakage may be shown at 0.25 µM melittin, it may be predicted that there is no selectivity for bacterial cells, and toxicity is very high.

On the other hand, the FP12-NH$_2$, FP13-NH$_2$, allD FP12-NH$_2$, and allD FP13-NH$_2$ peptides caused high dye leakage for a PC/PG (7:3, w/w) liposome mimicking a bacteria cell membrane, indicating high ability of disrupting a bacterial cell membrane. The FP12-NH$_2$, FP13-NH$_2$, allD FP12-NH$_2$, and allD FP13-NH$_2$ peptides selectively show almost no dye leakage for a PC/CH (1:1, w/w) liposome mimicking a red blood cell membrane in a mammal, which is consistent with low hemolytic activity. Therefore, it was seen that the peptides according to the present invention have an action mechanism of selectively disrupting a bacterial cell membrane.

Example 7: Evaluation of Stability Through Measurement of Proteolytic Enzyme Resistance of Peptide Stability in blood was confirmed through measurement of proteolytic enzyme resistance of the designed allD FP12-NH$_2$ and allD FP13-NH$_2$ peptides.

More specifically, to confirm resistance to three types of proteolytic enzymes such as trypsin, protease K, and chymotrypsin, a proteolytic enzyme was treated, and then the antibacterial activity of the peptides against *E. coli, A. baumannii* and *S. aureus* was measured.

As a result, it was confirmed that the allD FP12-NH$_2$ and allD FP13-NH$_2$ peptides designed through D-amino acid substitution, a non-natural amino acid, have much improved resistance to the proteolytic enzyme.

In the experimental data for *E. coli* and *A. baumannii* shown in Table 5, the allD FP12-NH$_2$ and allD FP13-NH$_2$ peptides showed antibacterial activity which is similar or reduced 2- to 4-fold compared to a case without proteolytic enzyme treatment, confirming that the peptides are highly functional peptides with very high stability.

In addition, in the experimental data for *S. aureus* shown in Table 6, it was also confirmed that the allD FP12-NH$_2$ and allD FP13-NH$_2$ peptides are highly functional peptides with very high stability.

TABLE 5

| MIC(uM) | allD FP12-NH2 | | allD FP13-NH2 | |
| --- | --- | --- | --- | --- |
| | MIC50 | MIC90 | MIC50 | MIC90 |
| *E. coli* | 2 | 4 | 2 | 4 |
| *E. coli* + 0.8 uM trypsin | 4 | 8 | 8 | 16 |
| *E. coli* + 0.8 uM protease K | 2 | 4 | 4 | 6(4~8) |
| *E. coli* + 0.8 uM Chymotrypsin | 4 | 8 | 2 | 6(4~8) |
| *A. baumannii* | 4 | 8 | 4 | 8 |
| *A. baumannii* + 0.8 uM trypsin | 8 | 32 | 8 | 32 |
| *A. Baumannii* + 0.8 uM protease K | 8 | 16 | 8 | 16 |
| *A. baumannii* + 0.8 uM Chymotrypsin | 8 | 16 | 8 | 16 |

TABLE 6

| MIC(uM) | all FP12-NH2 | | all FP13-NH2 | |
| --- | --- | --- | --- | --- |
| | MIC50 | MIC90 | MIC50 | MIC90 |
| *S. aureus* | 4 | 8 | 4 | 8 |
| *S. aureus* + 0.8 uM trypsin | 4 | 8 | 4 | 8 |
| *S. aureus* + 0.8 uM protease K | 4 | 8 | 4 | 8 |
| *S. aureus* + 0.8 uM Chymotrypsin | 4 | 8 | 4 | 8 |

Example 8: Antibiotic Effect of allD FP13-NH$_2$ on Standard Strain *E. coli* K1 and Two Types of Clinical Strains To evaluate the antibiotic activity of a peptide, the antibiotic effect and therapeutic effect of a peptide on *E. coli* K1 (standard strain), *E. coli* (ESBL) and carbapenem-resistant bacteria (carbapenem-resistant *Acinetobacter baummanii* (CRAB)) were verified through an animal experiment.

Except *E. coli* K1 (standard strain), *E. coli* (ESBL) and carbapenem-resistant bacteria (CRAB) were prepared from antibiotic-resistant bacteria obtained from patients with severe infection provided from the Division of Infection Disease of the Korea University Medical Center. The experimental bacteria were obtained by collecting 10 to 20 morphologically identical colonies, inoculated into a test tube containing 10 mL of a suitable liquid medium (Mueller Hinton Broth), and cultured in a 37° C. incubator for 12 hours. The liquid cell culture was placed in a sterilized cryo tube by 1 mL and stored at −80° C.

The test strain was cultured for 2 days in a 37° C. incubator [blood agar plate (BAP)], prepared in a Mueller Hinton Broth (MHB) liquid medium according to the amount of the inoculated strain ($1 \times 10^8$ or $8 \times 10^7$), and intraperitoneally injected (1 mL) into 6-week-old mice to induce infection. The mice were divided into groups per experiment (n=5 or 6 per group), and allD FP13-NH$_2$ mixed with a HARTMANN'S DEX solution (vehicle) was injected intraperitoneally into mice six times at 0, 1, 2, 3, 4, or 5 hours, followed by observing a survival rate at intervals of 12 hours for 3 days.

As a result, in a sepsis animal model into which each of *Escherichia coli* K1, *Escherichia coli* (ESBL), and carbapenem-resistant *Acinetobacter baumannii* was infected, an increase in survival rate (antibiotic effect) was confirmed within a concentration range from 3 mg to 12 mg per kg (FIG. 4). It was verified that the peptide designed in Example 1 also exhibits in vivo antibiotic and anti-septic effects in the standard strain and clinical strain-infected animal models.

Example 9: Acetate Salt Substitution of Peptide

To confirm the therapeutic and pharmaceutical effects of an acetate salt substitution of allD FP13-NH$_2$, a septic animal model induced by intraperitoneally administering each of the *Escherichia coli* (standard strain and ESBL) strains or a normal mouse was treated with the peptide allD FP13-NH$_2$ (AcOH). The antibiotic effect, the toxicity, and the inhibitory activity of anti-inflammatory cytokine IL-6 of the salt substitution with those of the same peptide at the end of trifluoroacetic acid (TFA) were compared.

An experimental method is as follows:

Six-week-old female ICR mice (SPF mice, Samtako) with an average body weight of 25 g were used as experimental animals. The experimental animals were provided with sterile feed and water and bred with less than 10 mice per cage, and a day/night cycle was 12 hours.

The test strain was cultured for 2 days in a 37° C. incubator [blood agar plate (BAP)], prepared in a Mueller Hinton Broth (MHB) liquid medium according to the amount of the inoculated strain ($1 \times 10^8$), and intraperitoneally injected ($1 \times 10^8$/200 μL) into 6-week-old mice to induce infection. The mice were divided into groups per experiment (n=5 or 6 per group), and intraperitoneally injected 6 times with allD FP13-NH$_2$ (TFA) and allD FP13-NH$_2$ (AcOH) mixed with HARTMANN'S DEX solution (vehicle) at 0, 1, 2, 3, 4, and 5 hours, followed by observing a survival rate at intervals of 12 hours.

To evaluate in vivo toxicity, the mice were divided into groups (n=5 or 6 per group) per experiment, and intraperitoneally treated six times with allD FP13-NH$_2$ (TFA) and allD FP13-NH$_2$ (AcOH) mixed with HARTMANN'S DEX solution (vehicle) at 0, 1, 2, 3, 4, or 5 hours, followed by observing a survival rate at intervals of 12 hours for 72 hours.

In addition, an IL-6 secretion test for bone marrow-derived dendrite cells (BMDCs) was carried out by comparatively analyzing cytokines secreted due to LPS 30 minutes after peptide treatment through the evaluation of LPS-mediated immune responses of allD FP13-NH$_2$ (TFA) and allD FP13-NH$_2$ (AcOH).

As a result, according to the antibiotic effect and toxicity test for a sepsis animal model (*E. coli* ESBL-induced model), since ED50 is approximately 1 mpk (mg/kg), LD50 is 80 mpk, and a ratio of a drug dose exhibiting toxicity to a drug dose for exhibiting a desired response (therapeutic index=LD50/ED50) is greater than 80, it is expected that a sufficient safety margin will be ensured, confirming that there is an excellent possibility of developing a novel antiseptic drug. In addition, it was confirmed that allD FP13-NH$_2$ (AcOH) significantly reduces the secretion of IL-6 increased due to LPS (FIGS. 5A to 5C).

Example 10: Evaluation of Antibacterial Activity of allD-Type Peptide Against Three Types of Gram-Positive Bacteria (Two Types of *S. aureus* and *S. epidermidis*)

To analyze the antibacterial activity of an allD-type peptide against gram-positive bacteria, the antibacterial activity against three types of gram-positive bacteria (two types of *S. aureus* and *S. epidermidis*) was confirmed.

To measure minimum inhibitory concentrations (MIC$_{50}$, minimum concentration for killing 50% of bacteria; MIC$_{100}$, minimum concentration required for completely killing bacteria), an antibacterial activity experiment method was evaluated.

More specifically, 100 μL of a medium was dispensed into each well of a 96-well plate, and in the first column, an antibiotic and a peptide in 200 μL of the medium were dispensed. 1/2 serial dilution was performed from columns 1 to 11 and three types of gram-positive bacteria (two types of *S. aureus* and *S. epidermidis*) which had been previously cultured were diluted (OD$_{600\ nm}$ value in dilution: approximately 0.0025) and dispensed into each well. The plate was incubated in a 37° C. incubator for 4 hours, and measured at OD$_{600\ nm}$. A bacterial growth rate was determined as 100% with the OD$_{600\ nm}$ value of a blank (well containing only medium and bacteria), and the concentrations of the antibiotic and peptide having an OD$_{600\ nm}$ value at which the growth inhibition rate was 50% or 100% were determined to calculate MIC$_{50}$ and MIC$_{100}$ values.

Consequently, as a result of analyzing antibacterial activity against gram-positive bacteria, it was confirmed that three types of peptides (allD FP12-NH$_2$, allD FP13-NH$_2$, and allD FP21-NH$_2$) to which an non-natural amino acid and an amino acid isomer (allomeric D-type amino acid) were further introduced exhibit excellent antibacterial activity against gram-positive bacteria at the same level as melittin.

TABLE 7

| Drugs | *S. aureus* KCTC1621 | | *S. aureus* CCARM3708 | | *S. epidermidis* CCARM3709 | |
| --- | --- | --- | --- | --- | --- | --- |
| | MIC50 | MIC100 | MIC50 | MIC100 | MIC50 | MIC100 |
| allD-FP12-NH2 | 4 | 16 | 4 | 8 | 1 | 2 |
| allD-FP13-NH2 | 4 | 8 | 2 | 4 | <1 | <1 |
| allD-FP21-NH2 | 4 | 8 | 2 | 4 | 1 | 2 |
| Melittin | 1 | 3 | 0.5 | 1 | 0.5 | 1 |

Example 11: Measurement of Disruption Ability of Peptide Against Liposome Mimicking Gram-Positive Bacterial Cell Membrane To study the action mechanisms for FPT2-NH$_2$, FPT3-NH$_2$, allD FPT2-NH$_2$, and allD FP13-NH$_2$ peptides, the disruption ability of the peptides against a liposome mimicking a bacterial cell membrane was measured.

To perform an experiment of confirming whether the antibacterial action of a peptide exhibits an action mechanism of killing bacteria by targeting the cell membrane of gram-positive bacteria, a liposome consisting of EYPG/EYPC (6:4, w/w) mimicking the cell membrane of gram-positive bacteria, encapsulating a fluorescent dye, calcein, was manufactured for a dye leakage assay.

As a result, the, FP12-NH$_2$, FP13-NH$_2$, allD FP12-NH$_2$ and allD FP13-NH$_2$ peptides caused high dye leakage for an EYPG/EYPC (6:4, w/w) liposome mimicking a bacterial cell membrane, indicating excellent ability of disrupting a bacterial cell membrane. Therefore, it can be seen that the FP12-NH$_2$, FP13-NH$_2$, allD FP12-NH$_2$, and allD FP13-NH$_2$ peptides according to the present invention have an action mechanism of disrupting a gram-positive bacterial cell membrane (FIG. 6).

Example 12: Measurement of Gram-Positive Bacteria-Derived LTA and LPP Binding Ability of allD FP13-NH$_2$ The following experiment was carried out to confirm the action mechanism by confirming the antibacterial activity of a peptide against gram-positive bacteria.

The binding affinity to lipoteichoic acid (LTA) and lipoprotein (LPP), which are cell wall components of gram-positive bacteria (*S. aureus*), was confirmed through ITC analysis using allD FP13-NH$_2$.

The binding affinity was confirmed using the ITC analysis method, and the experimental method in Example 1 was applied mutatis mutandis.

As a result, it was confirmed that allD FP13-NH$_2$ binds to LTA and LPP, which are cell wall components of gram-positive bacteria. It was confirmed that LPP is included in LTA, but does not bind to LPP including mutated LTA, and it was expected that LPP plays a more important role in binding of FP13-NH$_2$ and LTA. Accordingly, it was confirmed that the LPP binding will be important in the mechanism of antibacterial activity of FP13-NH$_2$ against gram-positive bacteria.

The foregoing description of the present invention is for illustrative purposes only, and those of ordinary skill in the art to which the present invention pertains can understand that the exemplary embodiments disclosed herein can be easily modified into other specific forms without departing from the technical spirit or essential features of the present invention. Therefore, the exemplary embodiments described above should be interpreted as illustrative in all aspects and not restrictive.

INDUSTRIAL AVAILABILITY

The peptide according to the present invention not only inhibits the proliferation of standard bacteria and antibiotic-resistant bacteria, but also has an excellent effect of removing a bacteria-derived endotoxin, thereby exhibiting an excellent treatment effect against sepsis. Besides, when used in combination with antibiotics, the peptide may minimize the side effects caused by the antibiotic, and thus can be efficiently used for the prevention or treatment of sepsis. In addition, the peptide according to the present invention shows an excellent antibacterial activity selectively against gram-positive/negative bacteria, and thus may be effectively used in preventing or treating various infectious diseases caused by gram-positive/negative bacteria or an antibacterial composition against gram positive/negative bacteria. Moreover, since the peptide according to the present invention is not only safe for the human body, but also exhibits stability against a proteolytic enzymes, its usage might be expanded for a variety of purposes.

Sequence Listing Free Text
Hereinafter, the sequence listing will be provided as follows:
[SEQ ID NO:
Name of polypeptide
Amino acid sequence]

1
FP1(WT)
(SEQ ID NO: 1)
Lys Leu Gly Val Glu Ala Lys Arg Tyr Leu Asp

2
FP3
(SEQ ID NO: 2)
Lys Leu Gly Val Glu Ala Lys Arg Tyr Leu Arg

3
FP5
(SEQ ID NO: 3)
Leu Arg Leu Gly Val Glu Ala Lys Arg Tyr Leu Arg

4
FP6
(SEQ ID NO: 4)
Leu Arg Leu Gly Val Glu Leu Lys Arg Tyr Leu Arg

5
FP9
(SEQ ID NO: 5)
Lys Leu Gly Val Glu Ala Leu Arg Tyr Leu Asp

6
FP12-NH2
(SEQ ID NO: 6)
Arg Leu Arg Val Lys Leu Arg Arg Tyr Leu Arg

7
FP13-NH2
(SEQ ID NO: 7)
Lys Leu Arg Val Lys Leu Arg Arg Tyr Leu Arg 8
allD FP12-NH2
(SEQ ID NO: 8)
Arg Leu Arg Val Lys Leu Arg Arg Tyr Leu Arg 9
allD FP13-NH2
(SEQ ID NO: 9)
Lys Leu Arg Val Lys Leu Arg Arg Tyr Leu Arg 10
allD FP-13-9a-NH2
(SEQ ID NO: 10)
Lys Leu Arg Val Lys Leu Arg Arg Ala Leu Arg 11
allD FP-13-9w-NH2
(SEQ ID NO: 11)
Lys Leu Arg Val Lys Leu Arg Arg Trp Leu Arg 12
allD FP-13-9k-NH2
(SEQ ID NO: 12)
Lys Leu Arg Val Lys Leu Arg Arg Lys Leu Arg 13
allD FP13-NH2 (AcOH)
(SEQ ID NO: 13)
Lys Leu Arg Val Lys Leu Arg Arg Tyr Leu Arg 14
PEG-allD FP13-NH2 (AcOH)
(SEQ ID NO: 14)
Lys Leu Arg Val Lys Leu Arg Arg Tyr Leu Arg 15
FP12
(SEQ ID NO: 15)
Arg Leu Arg Val Lys Leu Arg Arg Tyr Leu Arg 16
FP13
(SEQ ID NO: 16)
Lys Leu Arg Val Lys Leu Arg Arg Tyr Leu Arg 17
allD FP21-NH2
(SEQ ID NO: 17)
Arg Leu Arg Val Lys Leu Arg Arg Trp Leu Arg 18
allD FP-13-9d-NH2
(SEQ ID NO: 18)
Lys Leu Arg Val Lys Leu Arg Arg Asp Leu Arg

---

The invention claimed is:

1. A polypeptide consisting of by the following general sequence formula:

$$L_n\text{-}X_1\text{-}L\text{-}X_2\text{-}V\text{-}X_3\text{-}X_4\text{-}X_5\text{-}R\text{-}X_6\text{-}L\text{-}X_7 \text{(SEQ ID NO:19)} \quad \text{[General Formula]}$$

In the general formula,
n is 0 or 1;
L is leucine;
V is valine;
R is arginine;
$X_1$ is lysine (K) or arginine (R);
$X_2$ is glycine (G) or arginine (R);
$X_3$ is glutamic acid (E) or lysine (K);
$X_4$ is alanine (A) or leucine (L);
$X_5$ is lysine (K), leucine (L), or arginine (R);
$X_6$ is tyrosine (Y), alanine (A), tryptophan (W), lysine (K) or aspartic acid (D); and
$X_7$ is aspartic acid (D) or arginine (R),
but in the general formula, a polypeptide comprising the sequence of KLGVEAKRYLD (SEQ ID NO:1) is excluded, and
wherein - is a peptide bond.

2. A polypeptide of claim 1, which is any one of 10 types of the polypeptides consisting of General Formulas 1) to 10):

1) a polypeptide consisting of the general formula (SEQ ID NO:2), in which
n is 0;
$X_1$ is lysine (K);
$X_2$ is glycine (G);
$X_3$ is glutamic acid (E);
$X_4$ is alanine (A);
$X_5$ is lysine (K);
$X_6$ is tyrosine (Y); and
$X_7$ is arginine (R), 2) a polypeptide consisting of the general formula (SEQ ID NO:3), in which
n is 1;
$X_1$ is arginine (R);
$X_2$ is glycine (G);
$X_3$ is glutamic acid (E);
$X_4$ is alanine (A);
$X_5$ is lysine (K);
$X_6$ is tyrosine (Y); and
$X_7$ is arginine (R), 3) a polypeptide consisting of the general formula (SEQ ID NO:4), in which
n is 1;
$X_1$ is arginine (R);
$X_2$ is glycine (G);
$X_3$ is glutamic acid (E);
$X_4$ is leucine (L);
$X_5$ is lysine (K);
$X_6$ is tyrosine (Y); and
$X_7$ is arginine (R), 4) a polypeptide consisting of the general formula (SEQ ID NO:5), in which
n is 0;
$X_1$ is lysine (K);
$X_2$ is glycine (G);
$X_3$ is glutamic acid (E);
$X_4$ is alanine (A);
$X_5$ is leucine (L);
$X_6$ is tyrosine (Y); and
$X_7$ is aspartic acid (D), 5) a polypeptide consisting of the general formula (SEQ ID NO:15), in which
n is 0;
$X_1$ is arginine (R);
$X_2$ is arginine (R);
$X_3$ is lysine (K);
$X_4$ is leucine (L);
$X_5$ is arginine (R);
$X_6$ is tyrosine (Y); and
$X_7$ is arginine (R), 6) a polypeptide consisting of the general formula (SEQ ID NO:16), in which
n is 0;
$X_1$ is lysine (K);
$X_2$ is arginine (R);
$X_3$ is lysine (K);
$X_4$ is leucine (L);
$X_5$ is arginine (R);
$X_6$ is tyrosine (Y); and
$X_7$ is arginine (R), 7) a polypeptide consisting of the general formula (SEQ ID NO:10), in which
n is 0;
$X_1$ is lysine (K);
$X_2$ is arginine (R);
$X_3$ is lysine (K);
$X_4$ is leucine (L);

X5 is arginine (R);
X6 is alanine (A); and
X7 is arginine (R),
8) a polypeptide consisting of the general formula (SEQ ID NO:11), in which
n is 0;
X1 is lysine (K);
X2 is arginine (R);
X3 is lysine (K);
X4 is leucine (L);
X5 is arginine (R);
X6 is tryptophan (W); and
X7 is arginine (R),
9) a polypeptide consisting of the general formula (SEQ ID NO:12), in which
n is 0;
X1 is lysine (K);
X2 is arginine (R);
X3 is lysine (K);
X4 is leucine (L);
X5 is arginine (R);
X6 is lysine (K); and
X7 is arginine (R), and
10) a polypeptide consisting of the general formula (SEQ ID NO: 17), in which
is 0;
X1 is arginine (R);
X2 is arginine (R);
X3 is lysine (K);
X4 is leucine (L);
X5 is arginine (R);
X6 is tryptophan (W); and
X7 is arginine (R).

3. The polypeptide of claim 1, which is alkylated, PEGylated or amidated at the end of the polypeptide.

4. The polypeptide of claim 1, wherein an amine group is added to the C terminus of the polypeptide.

5. An acetate salt of the polypeptide of claim 1.

6. A method for treating gram-positive or gram-negative bacterial infection, the method comprising:
administering to a subject in need thereof a composition comprising the polypeptide of claim 1.

7. The method of claim 6, wherein bacteria targeted by the composition are one or more selected from the group consisting of *Escherichia coli* DH5α, *Escherichia coli* K1, *Acinetobacter baumannii, Pseudomonas aeruginosa, Salmonella enteritidis, Salmonella typhimurium, Klebsiella pneumoniae, Staphylococcus aureus* and *Staphylococcus epidermidis*.

8. The method of claim 6, wherein bacteria targeted by the composition are one or more types of antibiotic-resistant bacteria selected from the group consisting of Extended Spectrum Beta Lactamase (ESBL) producing bacteria, carbapenem-resistant bacteria and colistin-resistant bacteria.

9. The method of claim 8, wherein the antibiotic-resistant bacteria are one or more selected from the group consisting of ESBL-producing *E. coli*, carbapenem resistant (CR)-*Acinetobactor baumannii*, CR-*Klebsiella pneumoniae*, CR-*Pseudomonas aeruginosa*, and colistin-resistant *Acinetobactor baumannii*.

10. A method of alleviating or treating an infectious disease caused by gram-positive or gram-negative bacterial infections or sepsis, the method comprising:
administering to a subject in need thereof a composition comprising the polypeptide of claim 1.

11. The method of claim 10, wherein the infectious disease is an infectious disease caused by gram-negative bacteria, which is selected from pneumonia, peritonitis, meningitis, wound infection, osteoarthritis, cholecystitis, urinary tract infection, endocarditis, myocarditis, pericarditis, arthritis, pharyngitis, gonorrhea, bacterial dysentery, enteritis, conjunctivitis, gastritis, otitis media, cystitis, and lymphangitis.

12. The method of claim 10, wherein the infectious disease is an infectious disease caused by gram-positive bacteria, which is selected from the group of consisting of laryngopharyngitis, impetigo, rheumatic fever, glomerulonephritis, neonatal sepsis, meningitis, pharyngitis, pneumonia, endocarditis, scarlet fever, SSTI (skin and soft tissue infection), deep soft tissue infection, empyema, and vaginitis.

13. A method of preparing a polypeptide, comprising:
culturing host cells transformed with a recombinant vector, wherein the recombinant vector comprises a polynucleotide that encodes a polypeptide of claim 1.

14. A method for treating gram-positive or gram-negative bacterial infection, the method comprising:
administering to a subject in need thereof a composition comprising the polypeptide of claim 5.

15. A method of alleviating or treating an infectious disease caused by gram-positive or gram-negative bacterial infection or sepsis, the method comprising:
administering to a subject in need thereof a composition comprising the polypeptide of claim 5.

* * * * *